(12) United States Patent
Lin et al.

(10) Patent No.: US 11,158,757 B2
(45) Date of Patent: Oct. 26, 2021

(54) OPTICAL SENSING DEVICE AND OPTICAL SENSING SYSTEM THEREOF COMPRISING A LIGHT RECEIVING DEVICE CAPABLE OF RECEIVING A FIRST RECEIVED WAVELENGTH HAVING A LARGEST EXTERNAL QUANTUM EFFICIENCY

(71) Applicant: EPISTAR CORPORATION, Hsinchu (TW)

(72) Inventors: Yi-Chieh Lin, Hsinchu (TW); Shiuan-Leh Lin, Hsinchu (TW); Yung-Fu Chang, Hsinchu (TW); Shih-Chang Lee, Hsinchu (TW); Chia-Liang Hsu, Hsinchu (TW); Yi Hsiao, Hsinchu (TW); Wen-Luh Liao, Hsinchu (TW); Hong-Chi Shih, Hsinchu (TW); Mei-Chun Liu, Hsinchu (TW)

(73) Assignee: EPISTAR CORPORATION, Hsinchu (TW)

( * ) Notice: Subject to any disclaimer, the term of this patent is extended or adjusted under 35 U.S.C. 154(b) by 147 days.

(21) Appl. No.: 16/697,340

(22) Filed: Nov. 27, 2019

(65) Prior Publication Data
US 2020/0168757 A1     May 28, 2020

(30) Foreign Application Priority Data

Nov. 27, 2018 (TW) .................. 107142154

(51) Int. Cl.
| | |
|---|---|
| H01L 31/0304 | (2006.01) |
| H01L 31/167 | (2006.01) |
| H01L 31/0232 | (2014.01) |
| H01L 31/02 | (2006.01) |
| H01L 25/16 | (2006.01) |

(Continued)

(52) U.S. Cl.
CPC ........ *H01L 31/167* (2013.01); *A61B 5/02141* (2013.01); *A61B 5/02427* (2013.01); *A61B 5/02433* (2013.01); *A61B 5/14546* (2013.01); *A61B 5/14552* (2013.01); *G01J 3/10* (2013.01); *H01L 25/167* (2013.01); *H01L 31/02005* (2013.01); *H01L 31/02325* (2013.01); *H01L 31/03046* (2013.01)

(58) Field of Classification Search
CPC ............ A61B 5/02427; A61B 5/02433; A61B 5/14552; A61B 5/14532; G01J 3/10; G01J 3/0272; H01L 25/167; H01L 31/03046; H01L 31/167; H01L 27/30; H01L 33/0062; H01L 51/42
USPC .............................................. 250/214.1, 239
See application file for complete search history.

(56) References Cited

U.S. PATENT DOCUMENTS

| | | | | |
|---|---|---|---|---|
| 3,881,113 A | * | 4/1975 | Rideout ................. | H01L 31/173 250/551 |
| 2017/0311825 A1 | | 11/2017 | Weekly et al. | |
| 2017/0325698 A1 | | 11/2017 | Allec et al. | |

FOREIGN PATENT DOCUMENTS

WO      2017173339      10/2017

* cited by examiner

*Primary Examiner* — Que Tan Le

(57) ABSTRACT

This disclosure discloses an optical sensing device. The device includes a carrier body; a first light-emitting device disposed on the carrier body; and a light-receiving device including a group III-V semiconductor material disposed on the carrier body, including a light-receiving surface having an area, wherein the light-receiving device is capable of receiving a first received wavelength having a largest external quantum efficiency so the ratio of the largest external quantum efficiency to the area is ≥13.

20 Claims, 23 Drawing Sheets

(51) Int. Cl.
*A61B 5/024* (2006.01)
*A61B 5/021* (2006.01)
*A61B 5/1455* (2006.01)
*A61B 5/145* (2006.01)
*G01J 3/10* (2006.01)

| Item | Control Group 1 | Control Group 2 | Implementation Group 1 | Implementation Group 2 |
|---|---|---|---|---|
| Size | 110mil*110mil | 80mil*80mil | 80mil*80mil | 100mil*100mil |
| PI Value | 0.86% | 0.64% | 0.84% | 1.56% |
| N(%) | 0.11 | 0.16 | 0.21 | 0.24 |

OPTICAL SENSING DEVICE AND OPTICAL SENSING SYSTEM THEREOF COMPRISING A LIGHT RECEIVING DEVICE CAPABLE OF RECEIVING A FIRST RECEIVED WAVELENGTH HAVING A LARGEST EXTERNAL QUANTUM EFFICIENCY

BACKGROUND

1. Technical Field

The present disclosure relates to an optical sensing device, and in particular to a non-invasive optical sensing device for detecting the physiological signals in the blood.

2. Description of the Related Art

In the fast-paced life, people are gradually more eager to monitor the physiological indices which are related to their body health in-situ. On the one hand, it is useful for the early detection and early treatment; on the other hand, it is useful for the in-situ monitoring of the physical condition during exercise.

Variety of physiological signals, such as the heart rhythm, the blood oxygen level, the blood sugar level, and the blood pressure, can be detected by a non-invasive optical sensing device. By approaching the non-invasive optical sensing device to the skin surface and irradiating the skin with a specific measuring light, the measuring light penetrates the skin to the cells and blood vessels in the body. With the properties of light absorption, light scattering, and light reflection, the optical sensing device can receive a portion of the returned measuring light and get the physiological indices by measuring and analyzing the returned measuring light. However, when people act or exercise, the relative position and the distance between the optical sensing device and the skin is affected that causes unstable returned measuring light and the inaccurate result. Therefore, if a light-receiving device in the optical sensing device has a high detection limit and a high signal to noise ratio, the accuracy and the stability of the optical sensing device can be enforced.

SUMMARY OF THE DISCLOSURE

The present disclosure provides an optical sensing device having a high detection limit and a high signal to noise ratio.

This disclosure discloses an optical sensing device. The device includes a carrier body; a first light-emitting device disposed on the carrier body; and a light-receiving device including a group III-V semiconductor material disposed on the carrier body, including a light-receiving surface having an area, wherein the light-receiving device is capable of receiving a first received wavelength having a largest external quantum efficiency so the ratio of the largest external quantum efficiency to the area is ≥13.

BRIEF DESCRIPTION OF THE DRAWING

The accompanying drawing is included to provide easy understanding of the application and is incorporated herein and constitutes a part of this specification. The drawing shows the embodiments of the present disclosure and, together with the description, serves to illustrate the principles of the present disclosure.

DETAILED DESCRIPTION OF THE EMBODIMENTS

Embodiments of the present disclosure now will be described more fully hereinafter with reference to the accompanying drawings, in which embodiments of the disclosure are shown. This disclosure may, however, be embodied in many different forms and should not be construed as limited to the embodiments set forth herein. Rather, these embodiments are provided so that this disclosure will be thorough and complete, and willfully convey the scope of the disclosure to those skilled in the art. Like numbers refer to like elements throughout.

Figure 1A:
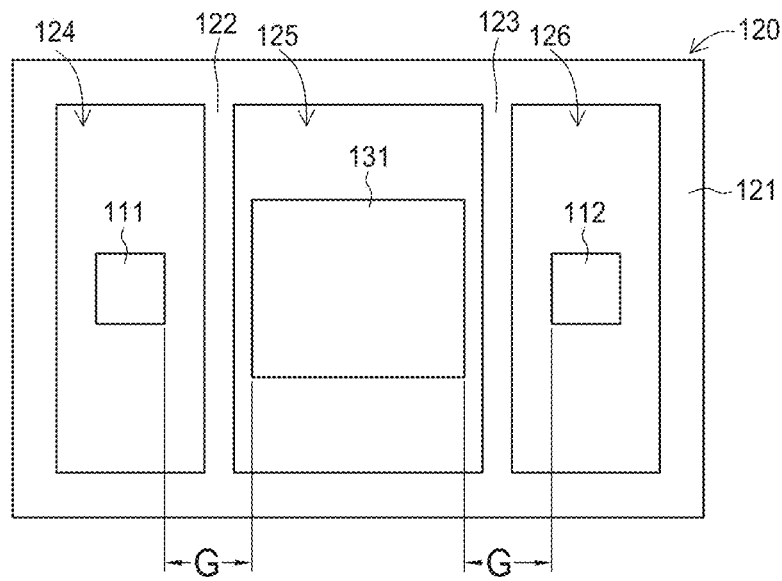
FIG. 1A is a top view of an optical sensing device in accordance with one embodiment of the present disclosure.

FIG. 1A shows a top view of an optical sensing device 100 in accordance with one embodiment of the present disclosure. The optical sensing device 100 includes a carrier body 120, a light-receiving device 131, a first light-emitting device 111, and a second light-emitting device 112. The carrier body 120 includes a shell 121 and two block walls 122 and 123 to separate a first space 124, a second space 125, and a third space 126. The first space 124 is surrounded by the shell 121 and the block wall 122, the third space 126 is surrounded by the shell 121 and the block wall 123, and the second space 125 is located between the first space 124 and the third space 126 and surrounded by the block walls 122 and 123 and the shell 121. The light-receiving device 131 is in the second space 125, the first light-emitting device 111 is in the first space 124, and the second light-emitting device 112 is in the third space 126. The first light-emitting device 111 and the second light-emitting device 112 are located at the left side and the right side of the light-receiving device 131 and symmetric to each other with respect to the light-receiving device 131. The distance between the light-receiving device 131 and the first light-emitting device 111 and/or the second light-emitting device 112 is preferred to be as close as possible. In that case, when the optical sensing device needs to measure the physiological signals, it irradiates near the skin so it is easier for the light-receiving device 131 to receive the returned signal only from the reflected light of the measuring light which the first light-emitting device 111 and the second light-emitting device 112 irradiate toward the skin surface. In this embodiment, the size of the optical sensing device 100 is 4.35 mm×3.15 mm, and the gap G between the light-receiving device 131 and the first light-emitting device 111 or the second light-emitting device 112 is equal to or smaller than 1 mm. The area of the light-receiving device 131 is larger than that of the first light-emitting device 111 and that of the second light-emitting device 112. As shown in FIG. 1A, the appearances of all the light-receiving device 131, the first light-emitting device 111, and the second light-emitting device 112 are squares. The size of the light-receiving device is ≤100 mil×100 mil, such as 100 mil×100 mil, 80 mil×80 mil, 61 mil×105 mil, 61×81 mil, 47 mil×105 mil, 60 mil×60 mil, 50 mil×50 mil, 45 mil×45 mil, and 40 mil×40 mil. In another embodiment, the size of the light-receiving device is ≤80 mil×80 mil. The size of the light-emitting device is ≤25 mil×25 mil, such as 20 mil×20 mil, 18 mil×18 mil, 16 mil×16 mil, 14 mil×11 mil, and 8 mil×8 mil.

The light-receiving device 131 and the light-emitting devices 111 and 112 are individually located in the separated and isolated spaces. Therefore, the lights irradiated by the light-emitting devices 111 and 112 are not directly received by the light-receiving device 131 so the crosstalk arising therefrom can be avoided and the accuracy of the detection is not affected.

Figure 1B:
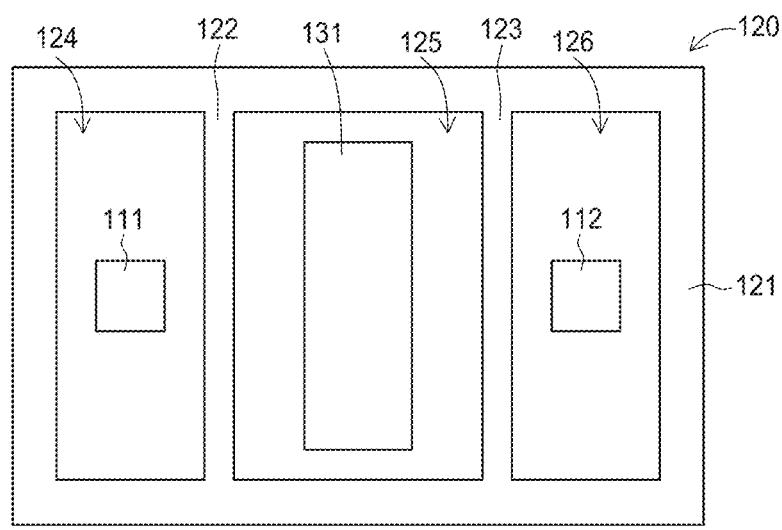
FIG. 1B is a top view of an optical sensing device in accordance with another embodiment of the present disclosure.

FIG. 1B shows a top view of an optical sensing device 101 in accordance with another embodiment of the present disclosure. Similar to the optical sensing device 100, the optical sensing device 101 includes a carrier body 120, a light-receiving device 131, a first light-emitting device 111, and a second light-emitting device 112. The carrier body 120 includes a shell 121 and two block walls 122 and 123 to separate a first space 124, a second space 125, and a third space 126. The light-receiving device 131 is in the second space 125, the first light-emitting device 111 is in the first space 124, and the second light-emitting device 112 is in the third space 126. The appearance of the light-receiving device 131 is a rectangle. The appearances of the first light-emitting device 111 and the second light-emitting device 112 are squares. The first light-emitting device 111 and the second light-emitting device 112 are located at the left side and the right side of the light-receiving device 131 and respectively symmetric to each other with respect to the long sides of light-receiving device 131.

Figure 1C:
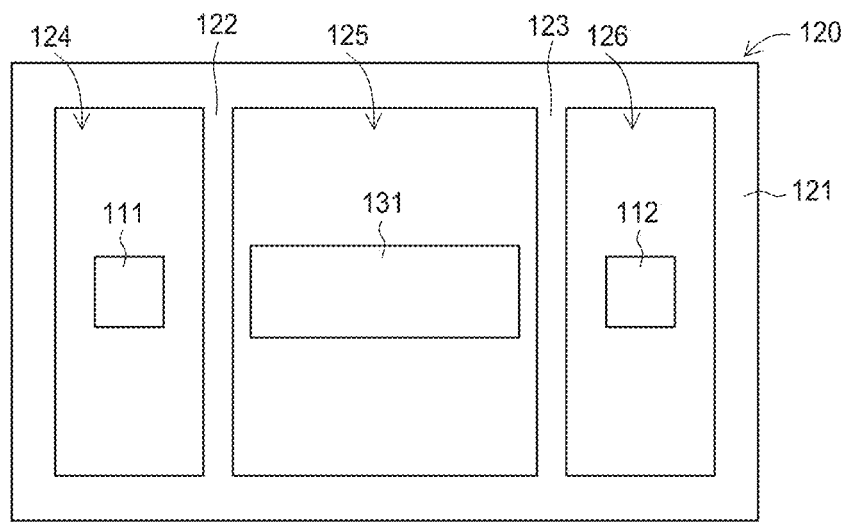
FIG. 1C is a top view of an optical sensing device in accordance with still another embodiment of the present disclosure.

FIG. 1C shows a top view of an optical sensing device 102 in accordance with still another embodiment of the present disclosure. Similar to the optical sensing device 100, the optical sensing device 102 includes a carrier body 120, a light-receiving device 131, a first light-emitting device 111, and a second light-emitting device 112. The carrier body 120 includes a shell 121 and two block walls 122 and 123 to separate a first space 124, a second space 125, and a third space 126. The light-receiving device 131 is in the second space 125, the first light-emitting device 111 is in the first space 124, and the second light-emitting device 112 is in the third space 126. The appearance of the light-receiving device 131 is a rectangle. The appearances of the first light-emitting device 111 and the second light-emitting device 112 are squares. The first light-emitting device 111 and the second light-emitting device 112 are located at the left side and the right side of the light-receiving device 131 and respectively symmetric to each other with respect to the short sides of light-receiving device 131. Besides, the structures of the first light-emitting device 111 and the second light-emitting device 112 are mirror images to each other with respect to the light-receiving device 131.

The material of the shell 121 and the block walls 122 and 123 can be a polymer or a resin, such as a thermoplastic polymer/resin, and a thermosetting polymer/resin. The thermoplastic polymer/resin can be polyphthalamide (PPA), polycyclohexylenedimethylene terephthalate (PCT), acrylonitrile butadiene styrene (ABS), polyetheretherketone (PEEK), and so on. The thermosetting polymer/resin can be epoxy molding compound (EMC), a silicone molding compound (SMC), and so on. Optionally, the material of the shell 121 and the block walls 122 and 123 can be opaque material, such as a light-absorbing material or a light-reflective material, so that the interference between the light-emitting device and the light-receiving device can be reduced.

The color of the light-absorbing material is preferred to be a dark color which reflects light less than the light-reflective material does, such as black, brown, or gray. The material of the light-absorbing material can be bismaleimide triazine resin (BT) with a material which can shield the visible light covering on the surface thereof. The visible-light-shielding material can be black ink (BT is light yellow), a metal, a resin, or graphite. The metal material can be chromium or nickel. The resin material can be polyimide (PI) or acrylate with a light-absorbing material such as carbon, titanium dioxide, or a dark dye dispersed therein. The light-absorbing material can also be a mixture of a matrix and a light-absorbing substance, wherein the matrix can be silicone-based, or epoxy-based, and the light-absorbing substance can be carbon, titanium dioxide, or a dark dye.

The light-reflective material can be a mixture of a matrix and a substance with high reflectivity. The matrix can be silicone-based or epoxy-based. The substance with high reflectivity can be titanium dioxide, silicon dioxide, aluminum oxide ($Al_2O_3$), $K_2TiO_3$, $ZrO_2$, ZnS, ZnO, MgO, and so on.

Figure 2A:
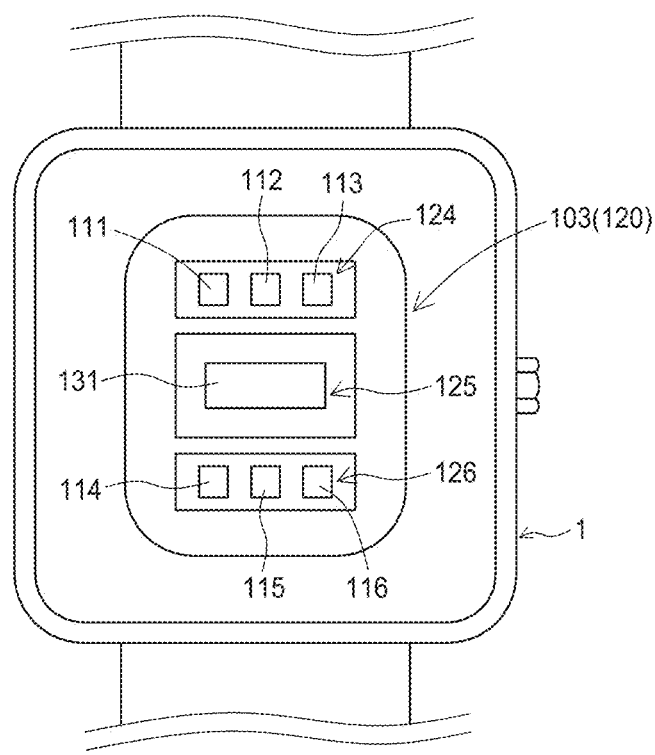
FIG. 2A is a schematic diagram of an optical sensing device disposed in a wearable device in accordance with one embodiment of the present disclosure.

FIG. 2A is a schematic diagram of an optical sensing device 103 disposed in a wearable device 1, such as a watch. The optical sensing device 103 is disposed at the center of the wearable device 1, and the structure of the optical sensing device 103 can be the optical sensing device 100, 101, or 102 mentioned above. The carrier body 120 includes a first space 124, a second space 125, and a third space 126. The second space 125 is located between the first space 124 and the third space 126. The first space 124 includes three light-emitting devices 111, 112, and 113 arranged in a line. The third space 126 includes three light-emitting devices 114, 115, and 116 arranged in a line. The second space 125 includes a light-receiving device 131. The first space 124, the second space 125, and the third space 126 are arranged in a line along a first direction (up-to-down direction). The light-emitting devices 111, 112, and 113 in the first space 124 are arranged in a line along a second direction (left-to-right direction). The light-emitting devices 114, 115, and 116 in the third space 126 are arranged in a line along the second direction (left-to-right direction). The first direction and the second direction are different and perpendicular to each other.

Figure 2B:
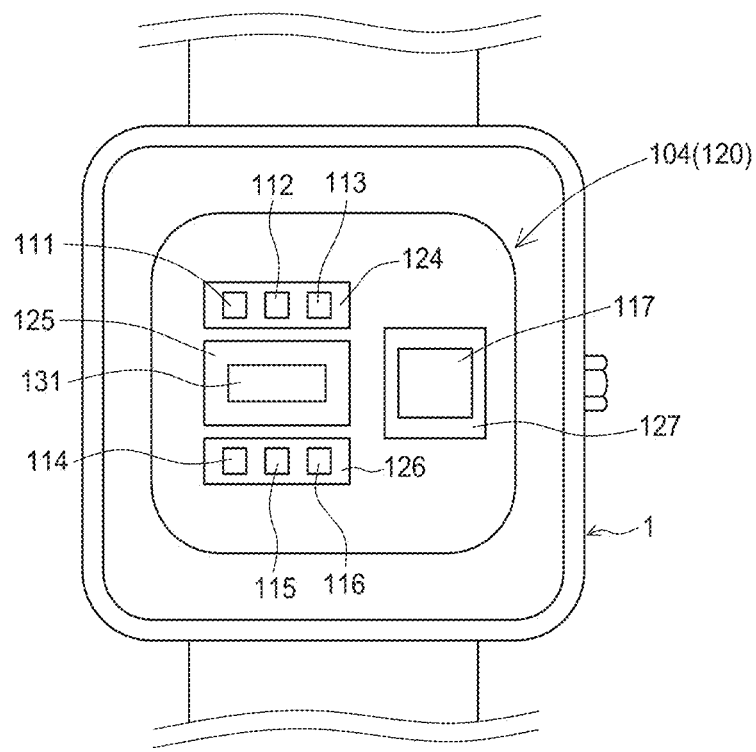
FIG. 2B is a schematic diagram of an optical sensing device disposed in a wearable device in accordance with another embodiment of the present disclosure.

FIG. 2B is a schematic diagram of an optical sensing device 104 disposed in a wearable device 1, such as a watch. The optical sensing device 104 is disposed at the center or near the center of the wearable device 1, and the structure of the optical sensing device 104 is similar to the optical sensing device 103. The carrier body 120 includes a first space 124, a second space 125, a third space 126, and a fourth space 127. The second space 125 is located between the first space 124 and the third space 126. The first space 124 includes three light-emitting devices 111, 112, and 113 arranged in a line. The third space 126 includes three light-emitting devices 114, 115, and 116 arranged in a line. The second space 125 includes a light-receiving device 131. The first space 124, the second space 125, and the third space 126 are arranged in a line along a first direction (up-to-down direction). The light-emitting devices 111, 112, and 113 in the first space 124 are arranged in a line along a second direction (left-to-right direction). The light-emitting devices 114, 115, and 116 in the third space 126 are arranged in a line along the second direction (left-to-right direction). The first direction and the second direction are different. For example, the first direction is perpendicular to or not parallel with the second direction. The fourth space 127 is located at the same side of the first space 124, the second space 125, and the third space 126 and is arranged in a line with the second space 125 along the second direction (left-to-right direction). The fourth space 127 includes a light-emitting device 117 which has an emitting wavelength larger than that of the light-emitting devices 111~116. For example, the light-emitting devices 111~116 emit the lights in the green wave band, and the light-emitting device 117 emits the light in the red wave band or the infrared (IR) wave band. The appearance of the light-emitting device 117 is a square or a rectangle and has an area larger than that of each of the light-emitting devices 111~116.

The light-receiving device in the present disclosure can be a photodiode having a photoelectric conversion efficiency equal to or larger than a predetermined value, so that it can convert the received photoenergy to an electric energy or a photocurrent. The material of the light-receiving device includes a semiconductor material, particular to a group III-V semiconductor material, such as InGaP for absorbing the wave band of 350~700 nm. GaAs for absorbing the wave band of 350~870 nm, or InGaAs for absorbing the wave band larger than 870 nm. For example, the receiving wave band of the light-receiving device 131 is 550~580 nm, which is a green wave band.

The light-emitting device in the present disclosure can be a light-emitting diode or a laser diode, wherein the light-emitting diode can be a chip with a single diode thereon or a chip with arrayed diodes (for high voltage operation) thereon. For example, the emitting wave bands of the light-emitting devices 111~116 are 480~600 nm, which are green wave bands.

The receiving wave band in the present disclosure means the wave band of the light emitted by the light-emitting device in the optical sensing device. For example, the wave band is a green wave band of 500~580 nm, a red wave band of 610~700 nm, and/or an IR wave band of 700~1700 nm. The light-emitting wave band of the light-emitting device is determined by the subject physiological signals for detection. For example, the green wave band is for detecting the heart rhythm and the blood pressure; the red wave band is for detecting the blood oxygen level; and the IR wave band is for detecting the blood oxygen level, the blood sugar level, and the blood lipid level. In the receiving wave band, the light-receiving device has a photoelectric conversion efficiency equal to or larger than a predetermined value, so that the light-receiving device can detect the light signals reflected from the subject for detection which absorbs the light emitted by the corresponding light-emitting device. The non-receiving wave band is the wave band outside the receiving wave band, and which includes the wave band larger and/or smaller than the receiving wave band. In one embodiment, the receiving wave band is a green wave band of 500~580 nm, and the non-receiving wave band is the wave band outside the green wave band such as the wave band smaller than 500 nm and/or the waveband larger than 580 nm. In another embodiment, the receiving wave band is a red wave band of 610~700 nm, and the non-receiving wave band is the wave band outside the red wave band such as the wave band smaller than 610 nm and/or the waveband larger than 700 nm. In still another embodiment, the receiving wave band is an IR wave band of 700~1700 nm, and the non-receiving wave band is the wave band outside the IR wave band such as the wave band smaller than 700 nm and/or the waveband larger than 1700 nm. In still another embodiment, the receiving wave band including two colors so that the receiving wave band can be used to detect variety of physiological signals. For example, the receiving wave band includes the green light and the red light; the receiving wave band includes the red light and the IR light; or the receiving wave band includes the green light, the red light, and the IR light.

Figure 3A:
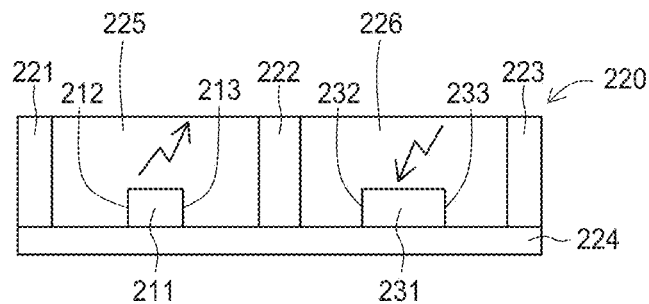
FIG. 3A is a partial cross-sectional view of an optical sensing device in accordance with one embodiment of the present disclosure.
Figure 3B:
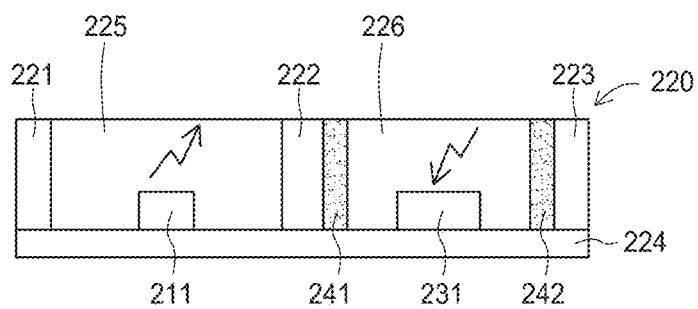
FIG. 3B is a partial cross-sectional view of an optical sensing device in accordance with another embodiment of the present disclosure.

FIGS. 3A~3M are partial cross-sectional views of an optical sensing device in accordance with embodiments of the present disclosure. FIG. 3A is a partial cross-sectional view of an optical sensing device 200, which includes a carrier body 220, a light-emitting device 211, and a light-receiving device 231. The optical sensing device 200 can be a part of the previous mentioned optical sensing devices 100, 101, and 102. The carrier body 220 includes a first block wall 221, a second block wall 222, a third block wall 223, and a carrier plate 224. The light-emitting device 211 and the light-receiving device 231 can be flip chips, upright horizontal chips, or upright vertical chips located on the carrier plate 224 and electrically connecting to the circuit on the carrier plate 224. The light-emitting device 211 is in the space 225 which is located between the first block wall 221 and the second block wall 222. The light-receiving device 231 is in the space 226 which is located between the second block wall 222 and the third block wall 223. The distance between the light-emitting device 211 and the first block wall 221 and the distance between the light-emitting device 211 and the second block wall 222 are larger than 0. The distance between the light-receiving device 231 and the second block wall 222 and the distance between the light-emitting device 231 and the third block wall 223 are larger than 0. In more detail, the light-emitting device 211 includes a first side surface 212 having a distance larger than 0 with the first block wall 221 and a second side surface 213 having a distance larger than 0 with the second block wall 222, and the light-receiving device 231 includes a first side surface 232 having a distance larger than 0 with the second block wall 222 and a second side surface 233 having a distance larger than 0 with the third block wall 223. The block walls 221, 222, and 223 are substantially perpendicular to the carrier plate 224.

The material of the block walls 221, 222, and 223 can be a light-reflective material or an opaque material such as a light-absorbing material which reflects light less than the light-reflective material does, and the details of the materials can be referred to the previous corresponding section. The carrier plate 224 can be a printed circuit board, an organic material, an inorganic material, or a bendable or a flexible material. The organic material can be a phenolic resin, a glass fiber, an epoxy resin, PI, or BT. The inorganic material can be an aluminum material or a ceramic material. The bendable or the flexible material can be polyethylene terephthalate (PET), PI, polyvinylidene fluoride (HPVDF), or ethylene tetrafluoroethylene (ETFE).

The side surfaces of the block walls in the optical sensing device facing the light-receiving device 231 can also include a light-absorbing material so that the reflection and the scattering of the irradiating light from the background noise can be reduced. As the partial cross-sectional view of an optical sensing device 201 shown in FIG. 3B, similar to the optical sensing device 200, the optical sensing device 201 includes a carrier body 220, a light-emitting device 211, and light-receiving device 231. The carrier body 220 includes a first block wall 221, a second block wall 222, a third block wall 223, and a carrier plate 224. The light-emitting device 211 and the light-receiving device 231 are located on the carrier plate 224. The light-emitting device 211 is in the space 225 which is located between the first block wall 221 and the second block wall 222. The light-receiving device 231 is in the space 226 which is located between the second block wall 222 and the third block wall 223. The inner surface of the second block wall 222 facing the light-receiving device 231 includes a light-absorbing layer 241 and the inner surface of the third block wall 223 facing the light-receiving device 231 includes a light-absorbing layer 242. Therefore, the light-receiving device 231 is in the space 226 of the carrier body 220 and surrounded by the light-absorbing layers 214 and 242. In another embodiment, in the space 226, the top surface of the carrier plate 224 which is not covered by the light-receiving device 231 can also include a light-absorbing layer which can reduce the background noise light reflected or scattered from the carrier plate 224 to enter the light-receiving device 231. In still another embodiment, every surface of the block walls 211, 212, and 213 includes a light-absorbing layer. It is worth noting that the figures only show the partial cross-sectional views of the optical sensing device 201. In the real structure, all the inner surfaces of the block walls facing the light-receiving device 231, similar to the inner surfaces of the second block wall 222 and the third block wall 223 shown in the figures, include light-absorbing layers.

Figure 3C:
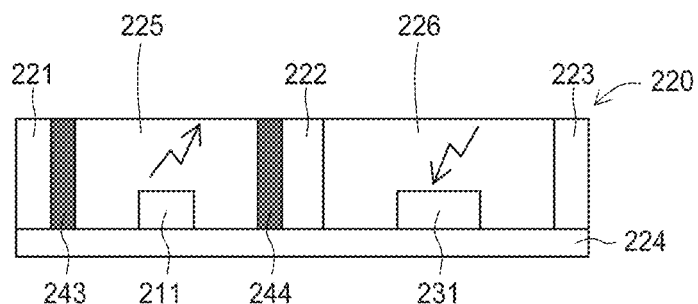
FIG. 3C is a partial cross-sectional view of an optical sensing device in accordance with still another embodiment of the present disclosure.

Among the surfaces of the block walls in the optical sensing device, the surfaces facing the space 225 where the light-emitting device 211 is located can also include a light-reflective material so that the light-emitting intensity can be enhanced. FIG. 3C discloses a partial cross-sectional view of an optical sensing device 202. Similar to the optical sensing device 200, the optical sensing device 202 includes a carrier body 220, a light-emitting device 211, and a light-receiving device 231. The carrier body 220 includes a first block wall 221, a second block wall 222, a third block wall 223, and a carrier plate 224. The light-emitting device 211 and the light-receiving device 231 are located on the carrier plate 224. The light-emitting device 211 is in the space 225 which is located between the first block wall 221 and the second block wall 222. The light-receiving device 231 is in the space 226 which is located between the second block wall 222 and the third block wall 223. The inner surface the first block wall 221 facing the light-emitting device 211 includes a light-reflective layer 243, and the inner surface the second block wall 222 facing the light-emitting device 211 includes a light-reflective layer 244. Therefore, the light-emitting device 211 is in the space 225 of the carrier body 220 and surrounded by the light-reflective layers 243 and 244. In another embodiment, in the space 225, the top surface of the carrier plate 224 which is not covered by the light-emitting device 211 can also include a light-reflective layer which can reflect and scatter the light irradiated toward the carrier plate 224 and redirect the reflected and scattered light upwardly to escape from the space 225. In still another embodiment, only a part of the block walls surrounding the light-emitting device 211 includes a light-reflective layer so that the light shape of the light escaping from the space 225 is asymmetric. For example, only the inner surface of the first block wall 221 facing the light-emitting device 211 includes a light-reflective layer 243 and the inner surface of the second block wall 222 facing the light-emitting device 211 does not include any light-reflective layer. Therefore, when the light escapes from the space 225, the light path is deviated toward the light-receiving device 231. In still another embodiment, every surface of the block walls 221, 222, and 223 includes a light-reflective layer. It is worth noting that the figures only show the partial cross-sectional views of the optical sensing device 202. In the real structure, all the inner surfaces of the block walls facing the light-emitting device 211, similar to the inner surfaces of the first block wall 221 and the second block wall 222 shown in the figures, include light-reflective layers.

Figure 3D:
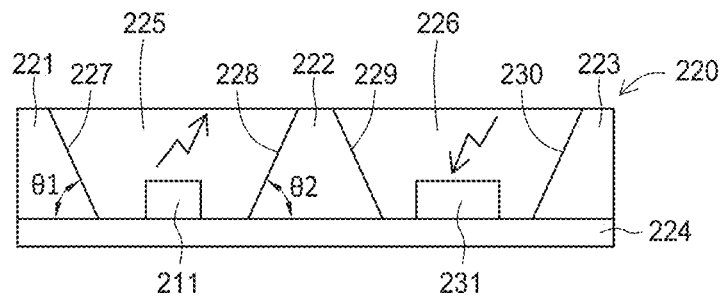
FIG. 3D is a partial cross-sectional view of an optical sensing device in accordance with still another embodiment of the present disclosure.

The side surface of the block wall facing the light-emitting device 211 in the optical sensing device can be an inclined plane in order to enhance the light extraction. The side surface of the block wall facing the light-receiving device 231 in the optical sensing device can also be an inclined plane in order to enhance the light-receiving area and the light-receiving amount. FIG. 3D discloses a partial cross-sectional view of an optical sensing device 203. Similar to the optical sensing device 200, the optical sensing device 203 includes a carrier body 220, a light-emitting device 211, and a light-receiving device 231. The carrier body 220 includes a first block wall 221, a second block wall 222, a third block wall 223, and a carrier plate 224. The light-emitting device 211 and the light-receiving device 231 are located on the carrier plate 224. The light-emitting device 211 is located in the space 225 which is located between the first block wall 221 and the second block wall 222. The light-receiving device 231 is located in the space 226 which is located between the second block wall 222 and the third block wall 223. The inner surface 227 of the first block wall 221 facing the light-emitting device 211 is not perpendicular to the carrier plate 224 and has a first inclined angle $\theta_1$ small than 90° relative to the carrier plate 224. The inner surface 228 of the second block wall 222 facing the light-emitting device 211 is not perpendicular to the carrier plate 224 and has a second inclined angle $\theta_2$ smaller than 90° relative to the carrier plate 224. Therefore, from the perspective of the cross-sectional view, the space 225 where the light-emitting device 211 is located has a shape with a wide upper portion and a narrow lower portion. In more detail, the width of the space 225 is getting larger along the direction away from the carrier plate 224. In the embodiment, the first inclined angle $\theta_1$ is substantially equal to the second inclined angle $\theta_2$. In another embodiment, the first inclined angle $\theta_1$ is different from the second inclined angle $\theta_2$. For example, the first inclined angle $\theta_1$ is larger than the second inclined angle $\theta_2$ (The center of the light shape on the light-emitting device 211 is deviated toward the first block wall 221), or the first inclined angle $\theta_1$ is smaller than the second inclined angle $\theta_2$ (The center of the light shape on the light-emitting device 211 is deviated toward the second block wall 222). The inner surface 229 of the second block wall 222 facing the light-receiving device 231 is not perpendicular to the carrier plate 224 and has an inclined angle smaller than 90° relative to the carrier plate 224. The inner surface 230 of the third block wall 223 facing the light-receiving device 231 is not perpendicular to the carrier plate 224 and has an inclined angle smaller than 90° relative to the carrier plate 224. Therefore, from the perspective of the cross-sectional view, the space 226 where the light-receiving device 231 is located has a shape with a wide upper portion and a narrow lower portion. In more detail, the width of the space 226 is getting larger along the direction away from the carrier plate 224. The block walls 221, 222, and 223 can include an opaque material which can include a light-absorbing material or a light-reflective material. The detailed description of the material can be referred to the previous corresponding sections. It is worth noting that the figures only show the partial cross-sectional views of the optical sensing device 203. In the real structure, all the inner surfaces of the block walls facing the light-emitting device 211, similar to the inner surfaces of the first block wall 221 and the second block wall 222, include inclined angles relative to the carrier plate 224; and all the inner surfaces of the block walls facing the light-receiving device 231, similar to the inner surfaces of the second block wall 222 and the third block wall 223, include inclined angles relative to the carrier plate 224.

Figure 3E:
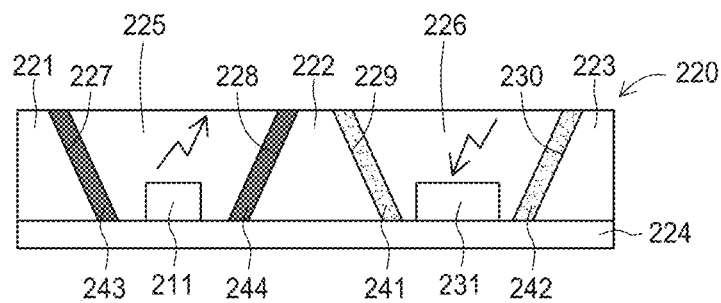
FIG. 3E is a partial cross-sectional view of an optical sensing device in accordance with still another embodiment of the present disclosure.

In the above embodiments, the light-emitting device 211 and the light-receiving device 231 can be flexibly combined with their photoelectric characteristics based on the environment where the optical sensing devices place. The block walls can have inclined angles relative to the carrier plate, the light-reflective layers and/or the light-absorbing layers can also be formed on the surfaces of the block walls. FIG. 3E discloses a partial cross-sectional view of an optical sensing device 204. Similar to the optical sensing device 203, the optical sensing device 204 includes a carrier body 220, a light-emitting device 211, and a light-receiving device 231. The carrier body 220 includes a first block wall 221, a second block wall 222, a third block wall 223, and a carrier plate 224. The light-emitting device 211 is in the space 225 which is located between the first block wall 221 and the second block wall 222. The light-receiving device 231 is in the space 226 which is located between the second block wall 222 and the third block wall 223. The inner surface 227 of the first block wall 221 facing the light-emitting device 211 has an inclined angle relative to the carrier plate 224 and includes a light-reflective layer 243. The inner surface 228 of the second block wall 222 facing the light-emitting device 211 has an inclined angle relative to the carrier plate 224 and includes a light-reflective layer 244. Therefore, from the perspective of the cross-sectional view, the space 225 where the light-emitting device 211 is located has a shape with a wide upper portion and a narrow lower portion. The inner surface 229 of the second block wall 222 facing the light-receiving device 231 has an inclined angle relative to the carrier plate 224 and includes a light-absorbing layer 241. The inner surface 230 of the third block wall 223 facing the light-receiving device 231 has an inclined angle relative to the carrier plate 224 and includes a light-absorbing layer 242. Therefore, from the perspective of the cross-sectional view, the space 226 where the light-receiving device 231 is located has a shape with a wide upper portion and a narrow lower portion. In still another embodiment, in the space 226, the top surface of the carrier plate 224 which is not covered by the light-receiving device 231 also includes a light-absorbing layer which can reduce the background noise light reflected or scattered from the carrier plate 224 to enter the light-receiving device 231. The top surface of the carrier plate 224 in the space 225 which is not covered by the light-emitting device 211 also includes a light-reflective layer which can reflect and scatter the light irradiated toward the carrier plate 224 and redirect the fleeted and scattered light upwardly to escape from the space 225.

Figure 3F:
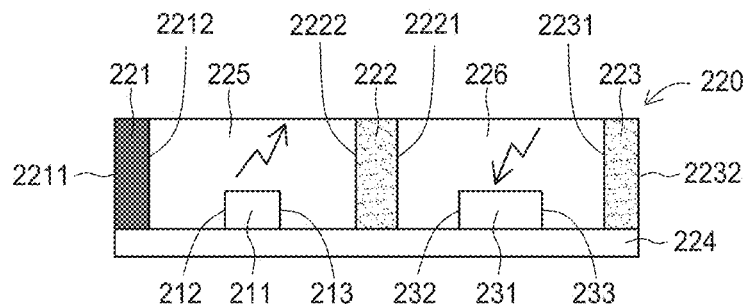
FIG. 3F is a partial cross-sectional view of an optical sensing device in accordance with still another embodiment of the present disclosure.

By different production process, the block wall and the light-reflective layer can be an integrated material, and/or the block wall and the light-absorbing layer can be an integrated material. FIG. 3F discloses a partial cross-sectional view of an optical sensing device 205. Similar to the optical sensing device 200, the optical sensing device 205 includes a carrier body 220, a light-emitting device 211, and a light-receiving device 231. The carrier body 220 includes a first block wall 221, a second block wall 222, a third block wall 223, and a carrier plate 224. The light-emitting device 211 and the light-absorbing device 231 are located on the carrier plate 224. The light-emitting device 211 is in the space 225 which is located between the first block wall 221 and the second block wall 222. The light-receiving device 231 is in the space 226 which is located between the second block wall 222 and the third block wall 223. A first outer surface 2211 of the first block wall 221 is the outermost surface of the optical sensing device 205. An inner surface 2212 faces the light-emitting device 211. The material of the first block wall 221 is a light-reflective material which can be included a mixture of a matrix and a substance with high reflectivity. The matrix can be silicone-based or epoxy-based. The substance with high reflectivity can be titanium dioxide, silicon dioxide. $Al_2O_3$, $K_2TiO_3$, $ZrO_2$, ZnS, ZnO, MgO, and so on. Therefore, the reflective indices of the inner and outer surfaces of the first block wall 221 are the same. A first inner surface 2221 of the second block wall 222 and an inner surface 2231 of the third block wall 223 face the light-receiving device 231. A second inner surface 2222 of the second block wall 222 faces the light-emitting device 211, and a second outer surface 2232 of the third block wall 223 can either face another light-receiving device or another light-emitting device of the optical sensing device (not shown). The material of the second block wall 222 and the third block wall 223 can be a light-absorbing material which reflects light less than the light-reflective material does. The color of the light-absorbing material is preferred to be a dark color which reflects light less than the light-reflective material does, such as black, brown, or gray. The material of the light-absorbing material can be BT with a material which can shield the visible light covering on the surface thereof. The visible-light-shielding material can be a black ink, a metal, a resin, or graphite. The metal material can be chromium or nickel. The resin material can be PI or acrylate with a light-absorbing material such as carbon, titanium dioxide, or a dark dye dispersed therein. The light-absorbing material can also be a mixture of a matrix and a light-absorbing substance, and the light-absorbing substance can be carbon, titanium dioxide, or a dark dye. In more detail, in the optical sensing device 205, the first side surface 212 of the light-emitting device 211 faces the first block wall 221 including the light-reflective material, and the second side surface 213 of the light-emitting device 211 faces the second block wall 222 including the light-absorbing material which reflects light less than the light-reflective material does. The first side surface 232 of the light-receiving device 231 faces the second block wall 222 including the light-absorbing material which reflects light less than the light-reflective material does, and the second side surface 233 of the light-receiving device 231 faces the third block wall 223 including the light-absorbing material which reflects light less than the light-reflective material does.

Figure 3G:
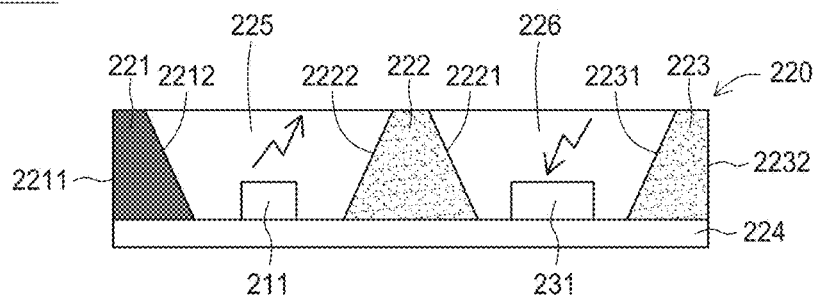
FIG. 3G is a partial cross-sectional view of an optical sensing device in accordance with still another embodiment of the present disclosure.

The outer surfaces of the block walls which face the light-emitting device and the light-receiving device in the optical sensing device 205 can be inclined planes. FIG. 3G discloses a partial cross-sectional view of an optical sensing device 206. A first outer surface 2211 of the first block wall 221 is the outermost surface of the optical sensing device 206. An inner surface 2212 faces the light-emitting device 211 and has an inclined angle which is not equal to 90° relative to the carrier plate 224. The first outer surface 2211 is substantially perpendicular to the carrier plate 24. In other words, the included angle of the first outer surface 2211 and the carrier plate 24 is different from the included angle of the inner surface 2212 and the carrier plate 24. The material of the first block wall includes a light-reflective material, and the detailed description of the material can be referred to the previous corresponding sections. The first inner surface 2221 of the second block wall 222 and the inner surface 2231 of the third block wall 223 face the light-receiving device 231. The second inner surface 2222 of the second block wall 222 faces the light-emitting device 211, and the second outer surface 2232 of the third block wall 223 can either face another light-receiving device or another light-emitting device of the optical sensing device (not shown). The material of the second block wall 222 and the third block wall 223 can be included a light-absorbing material which reflects light less than the light-reflective material does, and the detailed description of the material can be referred to the previous corresponding section. The first inner surface 2221 of the second block wall 222 and the inner surface 2212 of the second block wall 222 have inclined angles not equal to 90° relative to the carrier plate 224. Therefore, from the perspective of the cross-sectional view, the second block wall 222 has a shape with a wide upper portion and a narrow lower portion (trapezoid), and each of the spaces 225 and 226 has a shape with a narrow upper portion and a wide lower portion (inverted trapezoid). The space 226 has a shape with a wide upper portion and a narrow lower portion. The inner surface 2231 of the third block wall 223 has an inclined angle not equal to 90° relative to the carrier plate 224, and the second outer surface 2232 of the third block wall 223 is substantially perpendicular to the carrier plate 224. In another embodiment, the second outer surface 2232 of the third block wall 223 has an inclined angle not equal to 90° relative to the carrier plate 24.

Figure 3H:
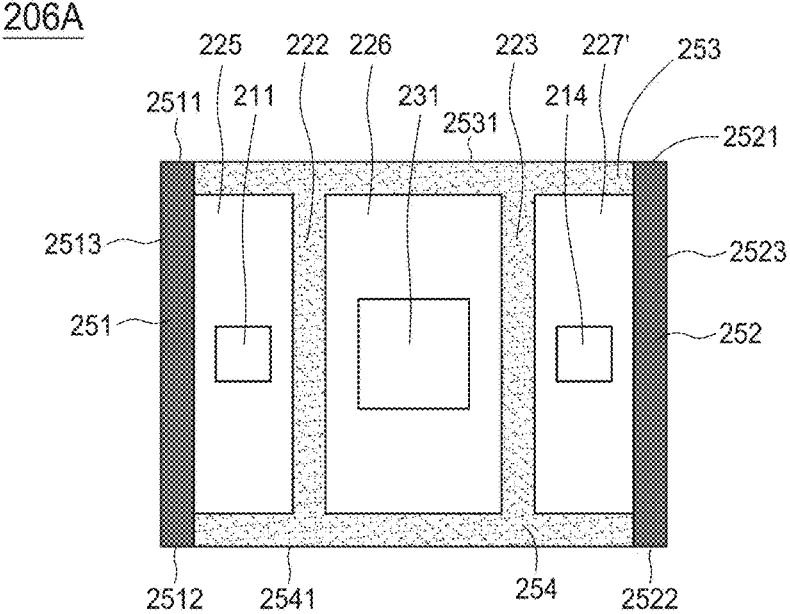
FIG. 3H is a top view of an optical sensing device in accordance with still another embodiment of the present disclosure.
Figure 3I:
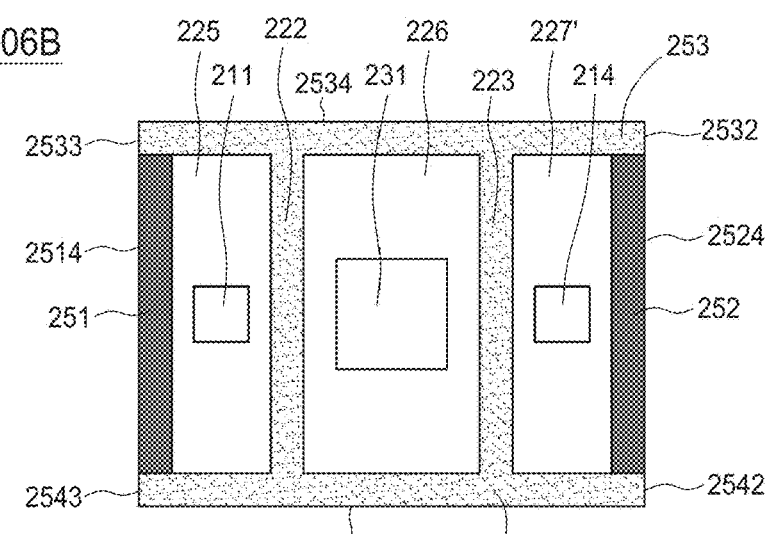
FIG. 3I is a top view of an optical sensing device in accordance with still another embodiment of the present disclosure.

FIGS. 3H~3I disclose the top views of the optical sensing devices when the first block wall 221 includes a light-reflective material. As shown in FIG. 3H, an optical sensing device 206A includes a first outermost block wall 251, a second block wall 222, a third block wall 223, a second outermost block wall 252, a third outermost block wall 253, and a fourth outermost block wall 254. The first outermost block wall 251, the second block wall 222, the third block wall 223, and the second outermost block wall 252 are parallel with each other and are disposed in a horizontal arrangement. The third outermost block wall 253 and the fourth outermost block wall 254 are parallel with each other and are disposed in a vertical arrangement. The third outermost block wall 253 is perpendicular to and connects to the first outermost block wall 251, the second block wall 222, the third block wall 223, and the second outermost block wall 252. The fourth outermost block wall 254 is perpendicular to and connects to the first outermost block wall 251, the second block wall 222, the third block wall 223, and the second outermost block wall 252. The first outermost block wall 251, the second block wall 222, the third outermost block wall 253, and the fourth outermost block wall 254 define a space 225 where the light-emitting device 211 is located. The second block wall 222, the third block wall 223, the third outermost block wall 253, and the fourth outermost block wall 254 define a space 226 where the light-receiving device 231 is located. The third block wall 223, the second outermost block wall 252, the third outermost block wall 253, and the fourth outermost block wall 254 define a space 227' where the light-emitting device 214 is located. The materials of the first outermost block wall 251 and the second outermost block wall 252 are light-reflective materials. The materials of the second block wall 222, the third block wall 223, the third outermost block wall 253, and the fourth outermost block wall 253 are light-absorbing materials which reflect light less than the light-reflective material does. The detailed description of the light-reflective material and the light-absorbing material can be referred to the previous corresponding sections.

From the perspective of the top view, the uppermost outer surface of the optical sensing device 206A can be separated into a left portion 2511, a middle portion 2531, and a right portion 2521. The middle portion 2521 is between the left portion 2511 and the right portion 2531. The left portion 2511 is the uppermost surface of the first outermost block wall 251 and the right portion 2521 is the uppermost surface of the second outermost block wall 252. The material of the middle portion 2531 includes a light-absorbing material which reflects light less than the light-reflective material does. The materials of the left portion 2511 and the right portion 2531 include light-reflective materials. The lowermost outer surface of the optical sensing device 206A can be separated into a left portion 2512, a middle portion 2541, and a right portion 2522. The middle portion 2541 is between the left portion 2512 and the right portion 2522. The left portion 2512 is the lowermost surface of the first outermost block wall 251 and the right portion 2522 is the lowermost surface of the second outermost block wall 252. The material of the middle portion 2541 includes a light-absorbing material which reflects light less than the light-reflective material does. The materials of the left portion 2512 and the right portion 2522 include light-reflective materials. The rightmost outer surface 2523 of the optical sensing device 206A is the outer surface of the second outermost block wall 252. Therefore, the rightmost outer surface 2523 includes a light-reflective material. The leftmost outer surface 2513 of the optical sensing device 206A is the outer surface of the first outermost block wall 251. Therefore, the leftmost outer surface 2513 includes a light-reflective material.

FIG. 3I is a top view of an optical sensing device 206B when the first block wall 221 includes a light-reflective material in another embodiment of the present disclosure. Similar to the optical sensing device 206A, optical sensing device 206B includes a first outermost block wall 251, a second block wall 222, a third block wall 223, a second outermost block wall 252, a third outermost block wall 253, and a fourth outermost block wall 254. The first outermost block wall 251, the second block wall 222, the third block wall 223, and the second outermost block wall 252 are parallel with each other and are disposed in a horizontal arrangement. The third outermost block wall 253 and the fourth outermost block wall 254 are parallel with each other and are disposed in a vertical arrangement. The third outermost block wall 253 is perpendicular to and connects to the first outermost block wall 251, the second block wall 222, the third block wall 223, and the second outermost block wall 252. The fourth outermost block wall 254 is perpendicular to and connects to the first outermost block wall 251, the second block wall 222, the third block wall 223, and the second outermost block wall 252. The first outermost block wall 251, the second block wall 222, the third outermost block wall 253, and the fourth outermost block wall 254 define a space 225 where the light-emitting device 211 is located. The second block wall 222, the third block wall 223, the third outermost block wall 253, and the fourth outermost block wall 254 define a space 226 where the light-receiving device 231 is located. The third block wall 223, the second outermost block wall 252, the third outermost block wall 253, and the fourth outermost block wall 254 define a space 227' where the light-emitting device 214 is located. The materials of the first outermost block wall 251 and the second outermost block wall 252 are light-reflective materials. The materials of the second block wall 222, the third block wall 223, the third outermost block wall 253, and the fourth outermost block wall 253 are light-absorbing materials which reflect light less than the light-reflective material does. The detailed description of the light-reflective material and the light-absorbing material can be referred to the previous corresponding sections.

From the perspective of the top view, the uppermost outer surface 2534 of the optical sensing device 206B is the uppermost surface 2534 of the third outermost block wall 253. Therefore, the uppermost outer surface 2534 includes a light-absorbing material which reflects light less than the light-reflective material does. The lowermost outer surface 2544 of the optical sensing device 206B is the lowermost surface 2544 of the fourth outermost block wall 254. Therefore, the lowermost outer surface 2544 includes a light-absorbing material which reflects light less than the light-reflective material does. The rightmost outer surface of the optical sensing device 206B includes a middle portion 2524, an upper portion 2532, and a lower portion 2542. The middle portion 2524 is between the upper portion 2532 and the lower portion 2542. The upper portion 2532 is the rightmost surface of the third outermost block wall 253 and the lower portion 2542 is the rightmost surface of the fourth block wall 254. The middle portion 2524 of the rightmost surface includes a light-reflective material and the upper portion 2532 and the lower portion 2542 include light-absorbing materials which reflect light less than the light-reflective material does. The leftmost outer surface of the optical sensing device 206B includes a middle portion 2514, an upper portion 2533, and a lower portion 2543. The middle portion 2514 is between the upper portion 2533 and the lower portion 2543. The upper portion 2533 is the leftmost surface of the third outermost block wall 253 and the lower portion 2543 is the leftmost surface of the fourth block wall 254. The middle portion 2514 of the leftmost wall includes a light-reflective material and the upper portion 2533 and the lower portion 2543 include light-absorbing materials which reflect light less than the light-reflective material does.

Each of the optical sensing devices shown in FIGS. 3H~3I includes only two outer block walls including different materials from the materials of the other block walls. In the manufacturing process, all the block walls can be made by the light-absorbing materials which reflect light less than the light-reflective material does first, then the two outer block walls facing the light-emitting devices are removed, and finally the two removed outer block walls are rebuilt by filling in the light-reflective materials so that the manufacturing process becomes easier.

Figure 3J:
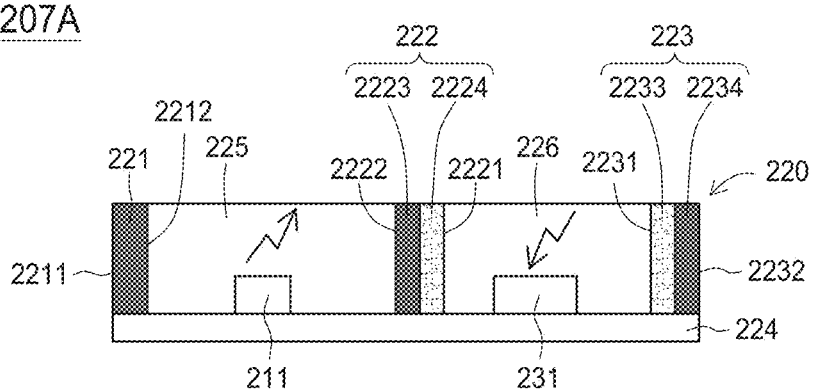
FIG. 3J is a partial cross-sectional view of an optical sensing device in accordance with still another embodiment of the present disclosure.

FIG. 3J discloses a partial cross-sectional view of an optical sensing device 207A in accordance with still another embodiment of the present disclosure. Similar to optical sensing device 205, the block wall and the light-reflective layer can be an integrated material, and the block wall and the light-absorbing layer can be an integrated material. The optical sensing device 207A includes a carrier body 220, a light-emitting device 211, and a light-receiving device 231. The carrier body includes a first block wall 221, a second block wall 222, a third block wall 223, and a carrier plate 224. The light-emitting device 211 and the light-receiving device 231 are disposed on the carrier plate 224. The light-emitting device 211 is in the space 225 which is located between the first block wall 221 and the second block wall 222. The light-receiving device 231 is in the space 226 which is located between the second block wall 222 and the third block wall 223. A first outer surface 2211 of the first block wall 221 is the outermost surface of the optical sensing device 207A. An inner surface 2212 faces the light-emitting device 211. The material of the first block wall 221 is a light-reflective material. Therefore, the reflective indices of the inner and the outer surfaces of the first block wall 221 are the same. The second block wall 222 includes a first portion 2223 and a second portion 2224 which are tightly adjacent to each other. The outer surface of the first portion 2223 is the second inner surface 2222 of the second block wall 222 facing the light-emitting device 211. The outer surface of the second portion 2224 is the first inner surface 2221 of the second block wall 222 facing the light-receiving device 231. The material of the first portion 2223 is the light-reflective material and the material of the second portion 2224 is the light-absorbing material which reflects light less than the light-reflective material does. Therefore, the reflective indices of two corresponding outer surfaces of the second block wall 222 are different. A second outer surface 2232 of the third block wall 223 can either face another light-receiving device or another light-emitting device (not shown), if the second outer surface 2232 faces another light-receiving device, the material of the third block wall 223 is the light-absorbing material which reflects light less than the light-reflective material does, and if the second outer surface 2232 faces another light-emitting device, as shown in FIG. 3F, the third block wall 223 is similar to the second block wall 222 and includes a first portion 2233 and a second portion 2234 which are tightly adjacent to each other. The outer surface of the first portion 2233 is the inner surface 2231 of the third block wall 223 facing the light-receiving device 231. The outer surface of the second portion 2234 is the second outer surface 2232 of the third block wall 223 facing another light-emitting device in the optical sensing device (not shown). The material of the first portion 2233 is a light-absorbing material which reflects light less than the light-reflective material does. The material of the second portion 2234 is the light-reflective material. Therefore, the reflective indices of two corresponding outer surfaces of the third block wall 223 are different.

Figure 3K:
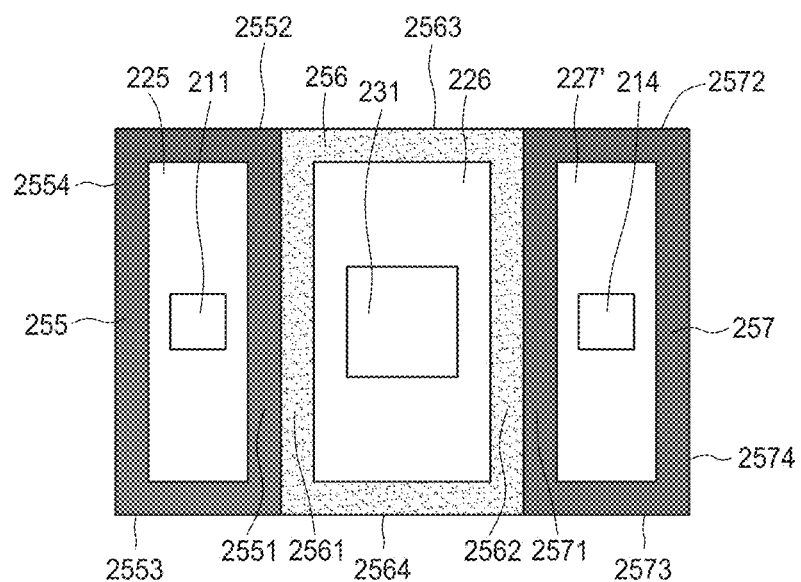
FIG. 3K is a top view of an optical sensing device in accordance with still another embodiment of the present disclosure.

FIG. 3K discloses a top view of an optical sensing device in accordance with an embodiment of the present disclosure. Similar to optical sensing device 207A shown in FIG. 3J, optical sensing device 207B shown includes a first block wall structure 255 which forms a space 225 where the light-emitting device 211 is located, a second block wall structure 256 which forms a space 226 where the light-receiving device 231 is located, and third block wall structure 257 which forms a space 227' where the light-emitting device 214 is located. The first block wall structure 255 is composed of the light-reflective material and surrounds the periphery of the light-emitting device 211. The second block wall structure 256 is composed of the light-absorbing material which reflects light less than the light-reflective material does and surrounds the periphery of the light-receiving device 231. The third block wall structure 257 is composed of the light-reflective material and surrounds the periphery of the light-emitting device 214. A side 2551 of the first block wall structure 255 near the second block wall structure 256 is tightly adjacent to a side 2561 of the second block wall structure 256 near the first block wall structure 255. A side 2562 of the second block wall structure 256 near the third block wall structure 257 is tightly adjacent to a side 2571 of the third block wall structure 257 near the second block wall structure 256.

From the perspective of the top view, the uppermost outer surface of the optical sensing device 207B includes a middle portion 2563, a left portion 2552, and a right portion 2572. The middle portion 2563 is between the left portion 2552 and the right portion 2572. The left portion 2552 is the upper surface of the first block wall structure 255, and the right portion 2572 is the upper surface of the third block wall structure 257. The material of the middle portion 2563 of the uppermost outer surface includes the light-absorbing material reflects light less than the light-reflective material does, and the materials of the left portion 2552 and the right portion 2572 include the light-reflective materials. The lowermost outer surface of the optical sensing device 207B includes a middle portion 2564, a left portion 2553, and a right portion 2573. The middle portion 2564 is between the left portion 2553 and the right portion 2573. The left portion 2553 is the lower surface of the first block wall structure 255, and the right portion 2573 is the lower surface of the third block wall structure 257. The material of the middle portion 2564 of the lowermost outer surface includes the light-absorbing material which reflects light less than the light-reflective material does, and the materials of the left portion 2553 and the right portion 2573 include the light-reflective materials. The rightmost outer surface 2574 of the optical sensing device 207B is the outer surface of the third block wall structure 257. Therefore, the material of the rightmost outer surface 2574 of the optical sensing device 207B includes the light-reflective material. The leftmost outer surface 2554 of the optical sensing device 207B is the outer surface of the first block wall structure 255. Therefore, the material of the leftmost outer surface 2554 of the optical sensing device 2073 includes the light-reflective material.

Figure 3L:
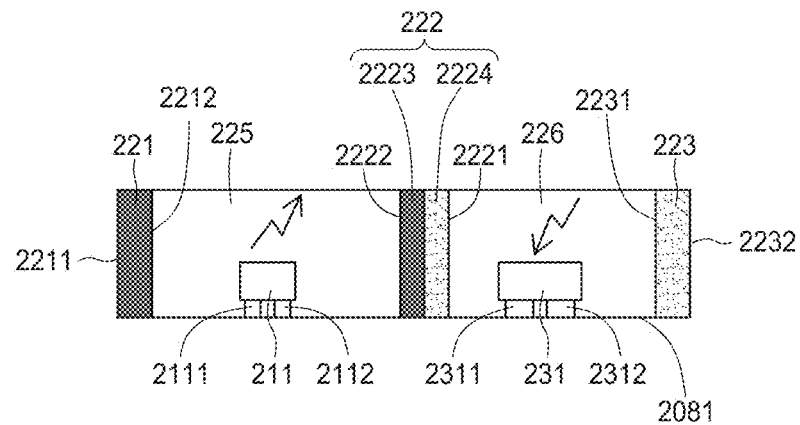
FIG. 3L is a partial cross-sectional view of an optical sensing device in accordance with still another embodiment of the present disclosure.

FIG. 3L discloses a partial cross-sectional view of an optical sensing device in accordance with still another embodiment of the present disclosure. Similar to optical sensing device 2074 shown in FIG. 3J, in FIG. 3L, the optical sensing device 208A includes a flip-chip type light-emitting device 211 and a flip-chip type light-receiving device 231. The light-emitting device 211 includes a first electrode 2111 and a second electrode 2112 located under the light-emitting device 211. The light-receiving device 231 includes a first electrode 2311 and a second electrode 2312 located under the light-receiving device 231. The light-emitting device 211 and the light-receiving device 231 are separated by the second block wall 222. The light-emitting device 211 is in the space 225 which is located between the first block wall 221 and the second block wall 222, and the light-receiving device 231 is in the space 226 which is located between the second block wall 222 and the third block wall 223. The material of the first block wall 221 is the light-reflective material. The second block wall 222 includes a first portion 2223 and a second portion 2224 which are tightly adjacent to each other. The outer surface of the first portion 2223 is a second inner surface 2222 of the second block wall 222 which faces the light-emitting device 211. The outer surface of the second portion 2224 is a first inner surface 2221 of the second block wall 222 which faces the light-receiving device 231. The material of the first portion 2223 is the light-reflective material. The material of the second portion 2224 is the light-absorbing material which reflects light less than the light-reflective material does. Therefore, the reflective indices of two corresponding outer surfaces of the second block wall 222 are different. The second outer surface 2232 of the third block wall 223 can face another light-receiving device or another light-emitting device in the optical sensing device (not shown). If the second outer surface 2232 faces another light-receiving device, the material of the third block wall 223 is the light-absorbing material which reflects light less than the light-reflective material does. If the second outer surface 2232 faces another light-emitting device, the second outer surface 2232 can be optionally tightly adjacent to another block wall portion which includes the light-reflective material (not shown). In this embodiment, the surfaces 2211, 2212, 2222, 2221, 2231, and 2232 of the first block wall 221, the second block wall 222, and the third block wall 223 are parallel to each other and disposed along a same direction.

The space 225 and the space 226 can be filled in a transparent encapsulating material to protect and to fix the light-emitting device 211 and the light-receiving device 231. The lower surfaces of the first electrode 2111 and the second electrode 2112 of the light-emitting device 211 and the lower surfaces of the first electrode 2311 and the second electrode 2312 of the light-receiving device 231 are exposed to the lower surface of the optical sensing device 208A. The material of the transparent encapsulating material can be silicone, epoxy, PI, benzocyclobutene (BCB), perfluorocyclobutane aromatic ether polymer (PFOB), SU-8, acrylic resin, poly-methyl methacrylate (PMMA), PET, polycarbonate (PC), polyetherimide, fluorocarbon polymer, $Al_2O_3$, SINR series photoresist, and spin-on glass (SOG).

Figure 3M:
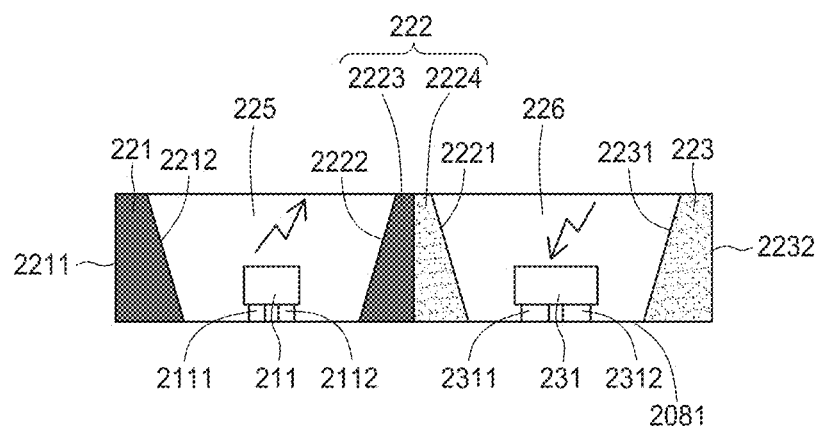
FIG. 3M is a partial cross-sectional view of an optical sensing device in accordance with still another embodiment of the present disclosure.

FIG. 3M discloses a partial cross-sectional view of an optical sensing device in accordance with still another embodiment of the present disclosure. Similar to optical sensing device 208A shown in FIG. 3L, in FIG. 3M, an optical sensing device 208B includes a flip-chip type light-emitting device 211 and a flip-chip type light-receiving device 231. The light-emitting device 211 includes a first electrode 2111 and a second electrode 2112, such as the positive electrode and the negative electrode, located under the light-emitting device 211. The light-receiving device 231 includes a first electrode 2311 and a second electrode 2312, such as the positive electrode and the negative electrode, located under the light-emitting device 231. The light-emitting device 211 and the light-receiving device 231 are separated by the second block wall 222. The light-emitting device 211 is in the space 225 which is located between the first block wall 221 and the second block wall 222, and the light-receiving device 231 is in the space 226 which is located between the second block wall 222 and the third block wall 223. The material of the first block wall 221 includes the light-reflective material so the first block wall 221 can reflect the light from the light-emitting device 211. The second block wall 222 includes a first portion 2223 and a second portion 2224 which are tightly adjacent to each other. The outer surface of the first portion 2223 is the second outer surface 2222 of the second block wall 222 which faces the light-emitting device 211. The outer surface of the second portion 2224 is the first inner surface 2221 of the second block wall 222 which faces the light-receiving device 231. The material of the first portion 2223 is the light-reflective material. The material of the second portion 2224 is the light-absorbing material which reflects light less than the light-reflective material does. Therefore, the reflective indices of two corresponding outer surfaces of the second block wall 222 are different. The second outer surface 2232 of the third block wall 223 can face another light-receiving device or another light-emitting device in the optical sensing device (not shown). If the second outer surface 2232 faces another light-receiving device, the material of the third block wall 223 is the light-absorbing material which reflects light less than the light-reflective material does. If the second outer surface 2232 faces another light-emitting device, the second outer surface 2232 can be optionally tightly adjacent to another block wall portion which includes the light-reflective material (not shown), The inner surface 2212 of the first block wall 221 facing the light-emitting device 211 has an inclined angle not equal to 90° relative to the lowermost surface 2081 of the optical sensing device 208B. The second outer surface 2222 of the second block wall 222 facing the light-emitting device 211 has an inclined angle not equal to 90° relative to the lowermost surface 2081 of the optical sensing device 208B. The first inner surface 2221 of the second block wall 222 facing the light-receiving device 231 has an inclined angle not equal to 90° relative to the lowermost surface 2081 of the optical sensing device 208B. The inner surface 2231 of the third block wall 223 facing the light-receiving device 231 has an inclined angle not equal to 90° relative to the lowermost surface 2081 of the optical sensing device 208B. Therefore, from the perspective of the cross-sectional view, the second block wall 222 has a shape with a narrow upper portion and a wide lower portion, and each of the spaces 225 and 226 has a shape with a wide upper portion and a narrow lower portion.

The space 225 and the space 226 can be filled in a transparent encapsulating material to protect and to fix the light-emitting device 211 and the light-receiving device 231. The lower surfaces of the first electrode 2111 and the second electrode 2112 of the light-emitting device 211 and the lower surfaces of the first electrode 2311 and the second electrode 2312 of the light-receiving device 231 are exposed to the lower surface of the optical sensing device 208B.

Figure 4A:
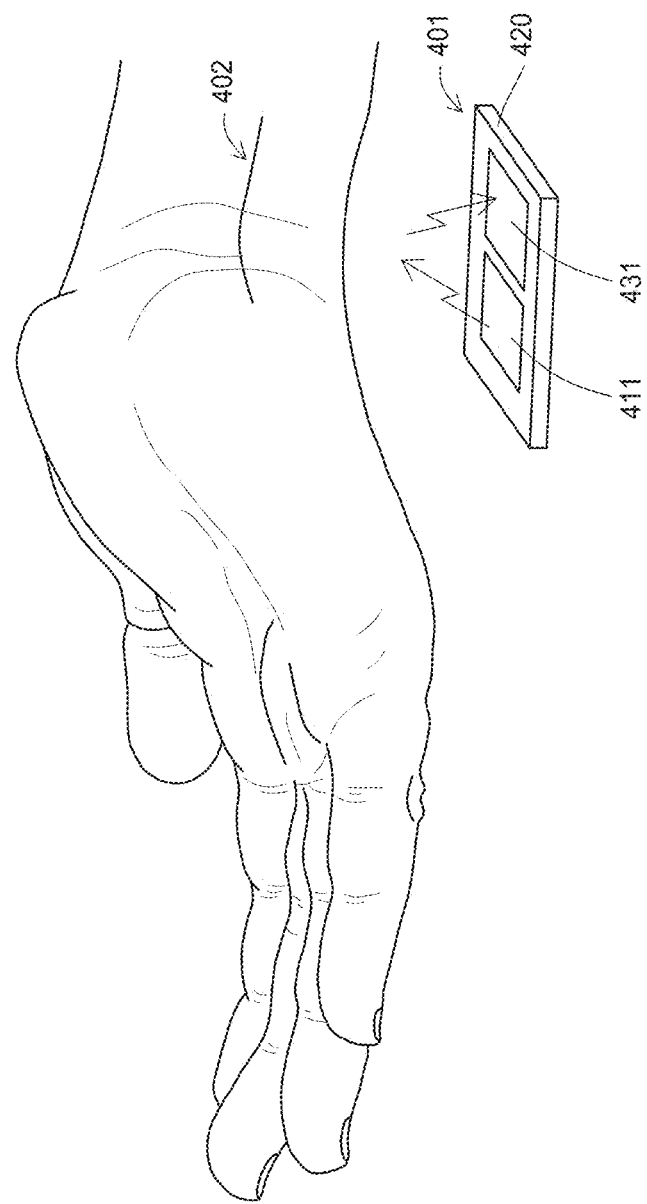
FIG. 4A is a schematic diagram of detecting by disposing an optical sensing device in accordance with an embodiment of the present disclosure on the wrist.

FIG. 4A is a schematic diagram of the detection by disposing a non-invasive optical sensing device on a portion of the human body such as the wrist. An optical sensing device 401 includes a light-emitting device 411 and a light-receiving device 431 disposed in a carrier body 420. The light-emitting device 411 emits a light toward the skin, and the light penetrates the subcutaneous tissue, the muscle, the body cell, the artery 402, the vein, and so on. When the light passes through the skin to the body cells and the bloods, the light can still penetrate, be absorbed, be reflected, and/or be scattered. By receiving the light scattered/reflected from the body cells and bloods by the light-receiving device, according to the variance of the scattered/reflected light, the physiological signals such as the heart rhythm, the blood oxygen level, the blood sugar level, and the blood pressure can therefore be retrieved. Taking the heart rhythm for example, the amount of the blood in the artery 402 changes regularly because the artery 402 contracts and relaxes according to the heartbeat. Therefore, the optical characteristic of the light scattered and reflected in the artery 402 due to the change of the blood volume is different from that of the light from other body cells. In other words, during the heartbeat period, the light returned from the skin is adjusted according to the change of the blood volume and is received by the light-receiving device 431. The change of the signals of the light are recorded as a photoplethysmogram (PPG), and one can therefore get the physiological information such as the heart rhythm therefrom. Although this illustration takes the wrist as an example, the optical sensing device of the present disclosure can also be applied to other portion of the skin surface such as the finger, the earlobe, the chest, and the forehead.

Figure 4B:
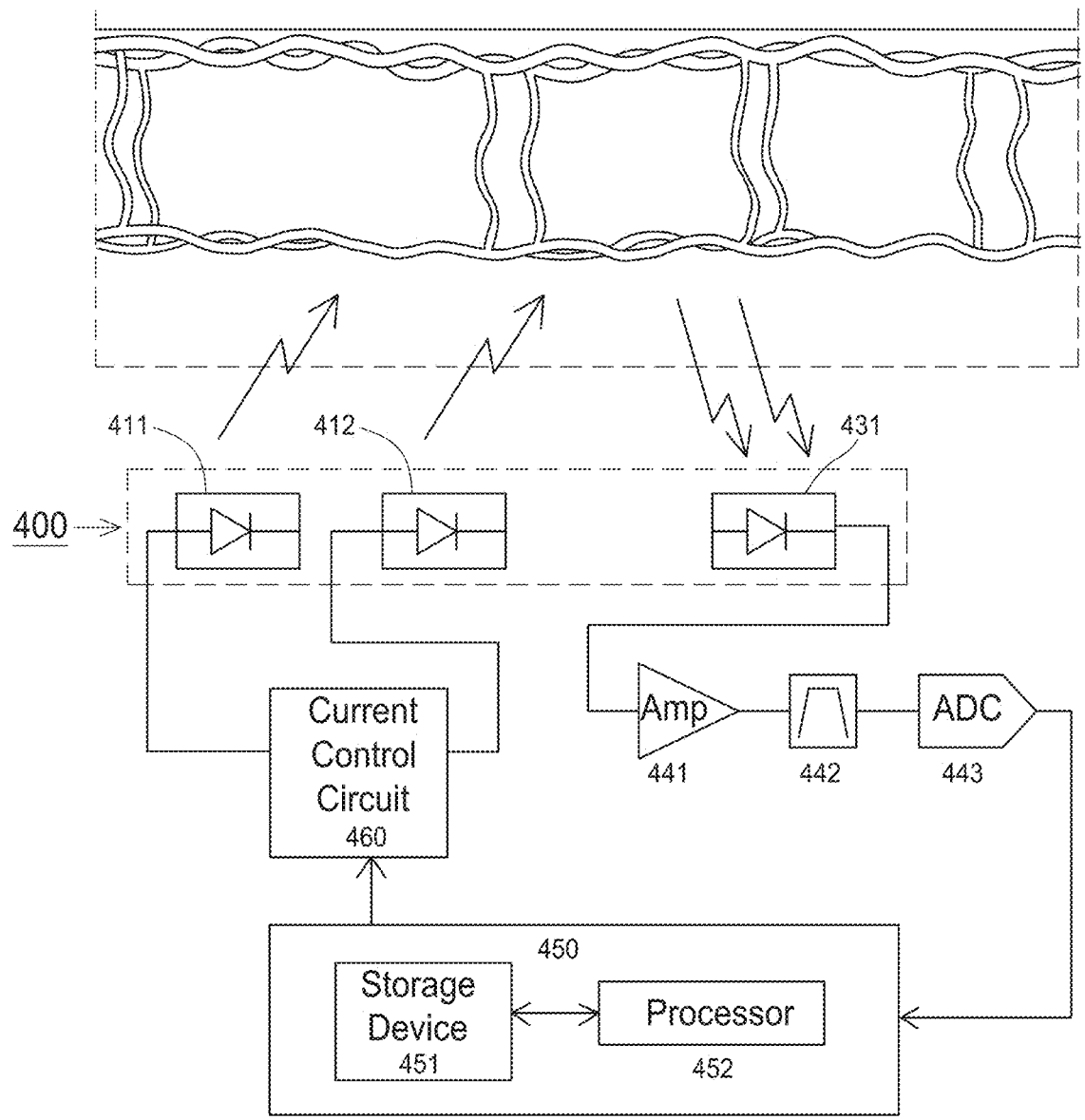
FIG. 4B is a circuit block diagram of an optical sensing system in accordance with one embodiment of the present disclosure.

FIG. 4B is a circuit block diagram of an optical sensing system in accordance with one embodiment of the present disclosure. The optical sensing system includes an optical sensing device 400 which includes a plurality of light-emitting devices 411 and 412 and a light-receiving device 431. A current control circuit 460 is coupled to the light-emitting devices 411 and 412 to drive them. An amplifier 441 is coupled to the light-receiving device 431 to receive and amplify the electric signals produced after the light-receiving device 431 received the light. A filter 442 is coupled to the output terminal of the amplifier 441 to eliminate the environmental noise. An ADC circuit 443 is coupled to the output terminal of the filter 442 to convert the analog electric signal to the digital electric signal which represents the magnitude of the light intensity. A signal processing module 450 is coupled to a current control circuit 460 and the ADC circuit 443, The signal processing module 450 includes a processor 452 and a storage device 451. The signal processing module 450 receives the electric signals from the ADC circuit 443 and the processor 452 stores, calculates, and analyzes the electric signals received by the light-receiving device 431. The processor 452 also outputs signals for the current control circuit 460 to adjust the light intensity emitted by the light-emitting devices 411 and 412. The detected result of the optical sensing system can be transmitted wirelessly through NFC, WiFi, Bluetooth, or other appropriate communication protocols to the remote display device such as the watch or the mobile phone.

Figures 5A, 5B:
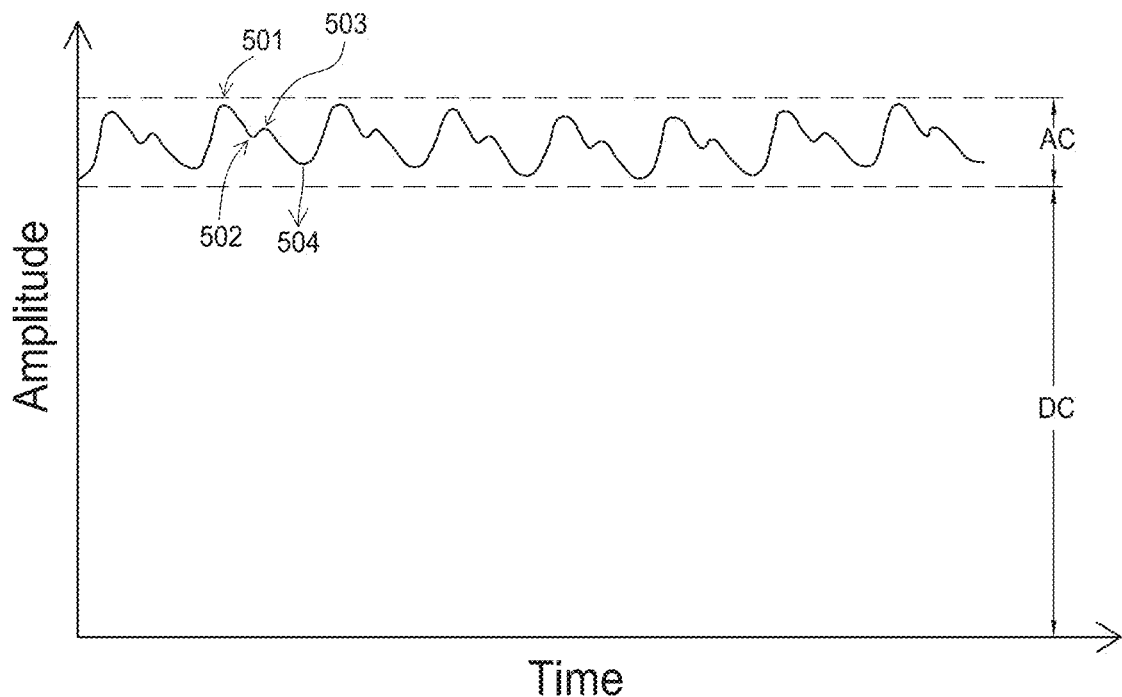
FIG. 5A is a photoplethysmography (PPG).
FIG. 5B is a comparison chart of the implementation groups of the light-receiving devices in accordance with the embodiments of the present disclosure and the control groups of other light-receiving devices in a same optical sensing system.

FIG. 5A shows the signal of the photoplethysmography (PPG). The PPG signal is related to the variance of the blood volume in the blood vessel. When the heart contracts and relaxes, the blood volume of the artery changes accordingly, and the intensity of the scattered/reflected light of the light penetrates the skin to the blood vessel changes. Therefore, the light intensity received by the light-receiving device produces corresponding waveforms in accordance with the contraction and relaxation of the heart. When the heart contracts and relaxes periodically, PPG can help to collect the physiological signals related the heart or the blood vessels, such as the heart rhythm. Referring to FIG. 5A, the vertical axis represents the normalized light intensity received by the optical sensing device (Amplitude). In one period in PPG, a first crest 501 represents the time the heart fully relaxed, a first trough 502 represents the demarcation point of the time between the heart relaxation and the heart contraction, a second crest 503 represents the blood refluxes when the heart changes from the relaxation to the contraction, and a second trough 504 represents the time the heart fully contracted. The changes of the slopes and the time-delayed distances between the first crest 501, the first trough 502, the second crest 503, and the second trough 504 represent the corresponding physiological phenomenon such as the blood oxygen concentration ($SpO_2$), the pulse rate, the respiratory rate, the stiffness index, the reflection index, the pulse transmit time (PTT), and the pulse wave velocity (PWV) of the heart and the blood vessels. Through the statistics of the time differences of the first crests 501 between the different and neighboring periods, the heartbeat period can be evaluated, and the heart rhythm can therefore be retrieved. The value of the PPG signal is a sum of a DC value which is not easy to change according to the time and an AC value which is changed according to the time. The AC value is the light intensities changed in accordance with the variance of the blood volume in the artery which is changed in accordance with the contraction and relaxation of the heart. The DC value is the scattered/reflected light intensity which affected by the difference of the skin color, the subcutaneous tissue, the cell, the vein, the bone, the muscle, and so on, and is not affected by the contraction and relaxation of the heart.

According to the DC value and the AC value of the PPG signals in FIG. 5A, one can get a perfusion index (PI), The definition of the PI value is AC/DC=PI (%). When the photoelectric conversion efficiency of the light-receiving device is higher, the PI value is larger, the values of the first crest 501, the first trough 502, the second crest 503, and the second trough 504 are more easily to be detected, and more physiological signals are more easily to be retrieved. If the PI value is not large enough, only the strongest first crests 501 of the PPG signals can be detected and therefore fewer physiological signals can be analyzed, for example, only the heart rhythm can be detected.

FIG. 5B is a comparison chart of the PI values of two implementation groups in accordance with two light-receiving devices in accordance with the embodiments (embodiment 1 and embodiment 2) of the present disclosure and the control groups (control group 1 and control group 2) in accordance with other light-receiving devices in a same optical sensing system. Both the materials of the control group 1 and the control group 2 include group IV semiconductor materials such as the silicon-based materials. The size of the optical sensing device of control group 1 is 110 mil×110 mil, the light-receiving area thereof is 7.56 mm², and PI=0.86%. The size of the optical sensing device of control group 2 is 80 mil×80 mil, the light-receiving area thereof is 4 mm², and PI=0.64%. Both the materials of the implementation group 1 and the implementation group 2 include group III-V semiconductor materials, such as InGaP and InGaAs. The size of the optical sensing device of implementation group 1 is 80 mil×80 mil, the light-receiving area thereof is 4 mm², and PI=0.86%. The size of the optical sensing device of implementation group 2 is 100 mil×100 mil, the light-receiving area thereof is 6.25 mm², and PI=1.56%. Because the materials of the implementation group 1 and the implementation group 2 include group III-V semiconductor materials, the photoelectric conversion efficiencies (external quantum efficiencies) thereof are higher than those of the control group 1 and the control group 2. In the case of similar sizes, the PI values of the implementation group 1 and the implementation group 2 are higher than those of the control group 1 and the control group 2. A ratio N of a light-receiving device is defined as N=PI (%)/the light-receiving area (mm²). N=0.11 in the control group 1, N=0.16 in the control group 2, N=0.21 in the implementation group 1, and N=0.24 in the implementation group 2. Therefore, each of the optical sensing systems in accordance with the embodiments of the present disclosure has a ratio N larger than 0.2.

The perfusion index is related to the race of the detected human and the part of the human body detected. The foregoing detected perfusion indices are obtained by the optical sensing device wore and measured on the wrist of an Asian person, wherein the optical sensing device has the light-absorbing wave band and the light-receiving wave band in the green wave band, such as a green wave band of 500~580 nm. During the measurement, the distance between the receiving surface of the light-receiving device in the optical sensing device and the skin of wrist is 1~2 mm.

Figure 6A:
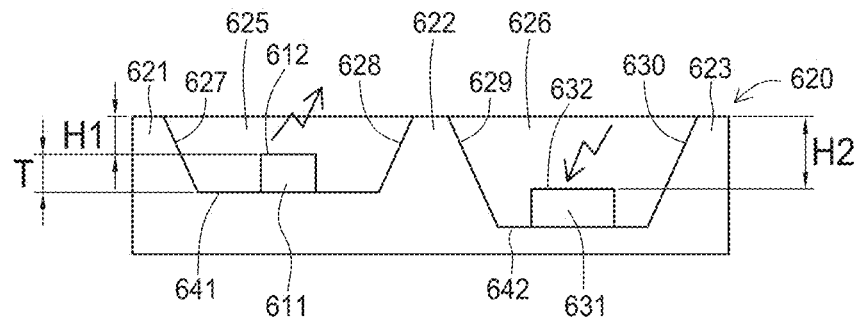
FIG. 6A is a partial cross-sectional view of an optical sensing device in accordance with still another embodiment of the present disclosure.

FIG. 6A is a partial cross-sectional view of an optical sensing device in accordance with still another embodiment of the present disclosure. Similar to the optical sensing device 203 disclosed in FIG. 3D, the optical sensing device 601 includes a carrier body 620, a light-emitting device 611, and a light-receiving device 631. The carrier body 620 includes a first block wall 621, a second block wall 622, and a third block wall 623. The light-emitting device 611 is in the space 625 which is located between the first block wall 621 and the second block wall 622. The light-receiving device 631 is in the space 626 which is located between the second block wall 622 and the third block wall 623. The carrier body 620 includes a first carrier surface 641 to carry the light-emitting device 611 and a second carrier surface 642 to carry the light-receiving device 631. An inner surface 627 of the first block wall 621 facing the light-emitting device 611 is not perpendicular to the first carrier surface 641 and has an obtuse angle relative to the first carrier surface 641. An inner surface 628 of the second block wall 622 facing the light-emitting device 611 is not perpendicular to the first carrier surface 641 and has an obtuse angle relative to the first carrier surface 641. Therefore, the space 625 where the light-emitting device 611 is located has a shape with a wide upper portion and a narrow lower portion from the perspective of the cross-sectional side view. In more detail, the width of the space 625 is getting larger along the direction away from the first carrier surface 641. An inner surface 629 of the second block wall 622 facing the light-receiving device 631 is not perpendicular to the second carrier surface 642 and has an inclined angle relative to the second carrier surface 642. An inner surface 630 of the third block wall 623 facing the light-receiving device 631 is not perpendicular to the second carrier surface 642 and has an inclined angle relative to the second carrier surface 642. Therefore, the space 626 where the light-receiving device 631 is located has a shape with a wide upper portion and a narrow lower portion from the perspective of the cross-sectional side view. In more detail, the width of the space 626 is getting larger along the direction away from the second carrier surface 642. The light-emitting device 611 has a light-emitting surface 612, and there is a distance H1 between the light-emitting surface 612 and the topmost surface of the carrier body 620. The light-receiving device 631 has a light-receiving surface 632, and there is a distance H2 between the light-receiving surface 632 and the topmost surface of the carrier body 620, wherein H1<H2. Therefore, comparing to the light-receiving device 631, the light-emitting device 611 is closer to the detected skin, and the light intensity incident to the skin can be enhanced. The distance between the first carrier surface 641 and the lowermost surface of the carrier body 620 is larger than distance between the second carrier surface 642 and the lowermost surface of the carrier body 620. In one embodiment, the light-emitting device 611 has a height T, and H2>H1+T. In another embodiment, the block walls 621, 622, and 623 are perpendicular to the first carrier surface 641 or the second carrier surface 642. In still another embodiment, similar to the embodiments shown in FIGS. 3B-3D, the inner surfaces 627, 628, 629, and 630 include the light-reflective layers or the light-absorbing layers. In still another embodiment, similar to the embodiments shown in FIGS. 3F~3M, the materials of the block walls 621, 622, and 623 include the light-reflective materials or the light-absorbing materials which reflect light less than the light-reflective material does.

Figure 6B:
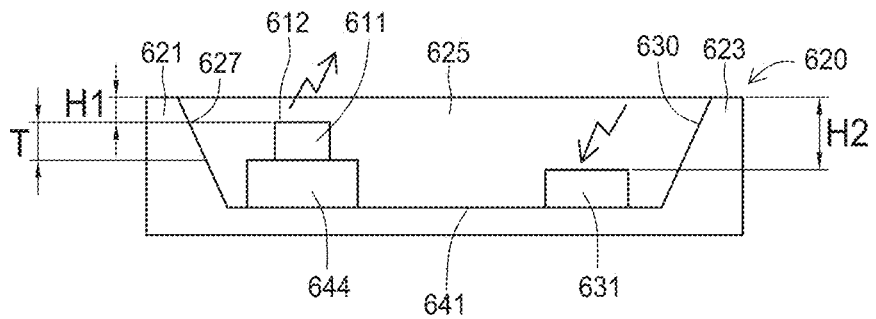
FIG. 6B is a partial cross-sectional view of an optical sensing device in accordance with still another embodiment of the present disclosure.

Because the emitting angle of the light-emitting device is smaller than 150°, for example, the emitting angle of the general light-emitting diode is about 120°, when the light-emitting surface of the light-emitting device is higher than the light-receiving surface of the light-receiving device, the degree the light emitted by the light-emitting device disturbing the light-receiving device is relatively small and even approaching zero. Therefore, in the optical sensing device, there is no need to use the block wall to separate the light-emitting device and the light-receiving device as shown in FIG. 6B. FIG. 6B is a partial cross-sectional view of an optical sensing device in accordance with still another embodiment of the present disclosure. The optical sensing device 602 includes a carrier body 620, a light-emitting device 611, and a light-receiving device 631. The carrier body 620 includes a first block wall 621, a third block wall 623, and a first carrier surface 641. The first carrier surface 641 carries the light-emitting device 611 and the light-receiving device 631. The light-emitting device 611 and the light-receiving device 631 are in the space 625 which is located between the first block wall 621 and the third block wall 623. An inner surface 627 of the first block wall 621 facing the light-emitting device 611 or the light-receiving device 631 is not perpendicular to the first carrier surface 641 and has an inclined angle relative to the first carrier surface 641. An inner surface 630 of the third block wall 623 facing the light-emitting device 611/the light-receiving device 631 is not perpendicular to the first carrier surface 641 and has an inclined angle relative to the first carrier surface 641. Therefore, the space 625 where the light-emitting device 611 and the light-receiving device 631 are located has a shape with a wide upper portion and a narrow lower portion from the perspective of the cross-sectional side view. In more detail, the width of the space 625 is getting larger along the direction away from the first carrier surface 641. The light-emitting device 611 has a light-emitting surface 612, and there is a distance H1 between the light-emitting surface 612 and the topmost surface of the carrier body 620. The light-receiving device 631 has a light-receiving surface 632, and there is a distance H2 between the light-receiving surface 632 and the topmost surface of the carrier body 620, wherein H1<H2. There is a connecting device 644 located between the first carrier surface 641 of the carrier body 620 and the light-emitting device 611. The connecting device 644 can be used to adjust the height of the light-emitting surface and the width of the connecting device 644 is larger than that of the light-emitting device 611. In one embodiment, the light-emitting device 611 has a height T, and H2>H1+T. In another embodiment, the block walls 621 and 623 are perpendicular to the first carrier surface 641. In still another embodiment, similar to the embodiments shown in FIGS. 3B-3D, the inner surfaces 627 and 630 include the light-reflective layers or the light-absorbing layers. The material of the connecting device 644 can be an insulating material which includes a plastic, such as polypropylene (PP), PC, polybutylene terephthalate (PBT), ABS, and a mixture of ABS and PC, or a ceramic material, such as $Al_2O_3$. The ceramic material can be made by the thick film process, the low temperature co-fired ceramic (LTCC) process, or the thin film process. The connecting device 644 can help the light-emitting device 611 to dissipate heat through the heat conduction.

Figure 6C:
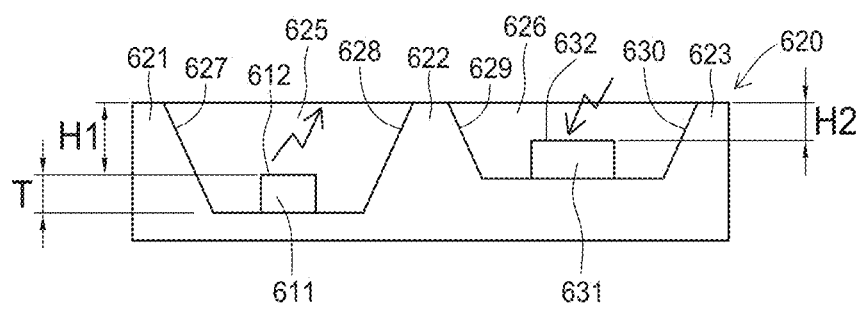
FIG. 6C is a partial cross-sectional view of an optical sensing device in accordance with still another embodiment of the present disclosure.

FIG. 6C is a partial cross-sectional view of an optical sensing device 603 in accordance with still another embodiment of the present disclosure. Similar to the optical sensing device 601 shown in FIG. 6A, an optical sensing device 603 includes a carrier body 620, a light-emitting device 611, and a light-receiving device 631. The light-emitting device 611 has a light-emitting surface 612, and there is a distance H1 between the light-emitting surface 612 and the topmost surface of the carrier body 620. The light-receiving device 631 has a light-receiving surface 632, and there is a distance H2 between the light-receiving surface 632 and the topmost surface of the carrier body 620, and H1>H2. Therefore, comparing to the light-emitting device 611, the light-receiving device 631 is closer to the detected skin, the light intensity received by the light-receiving device 631 can be enhanced, and the interference from the environmental light can be reduced.

Figure 6D:
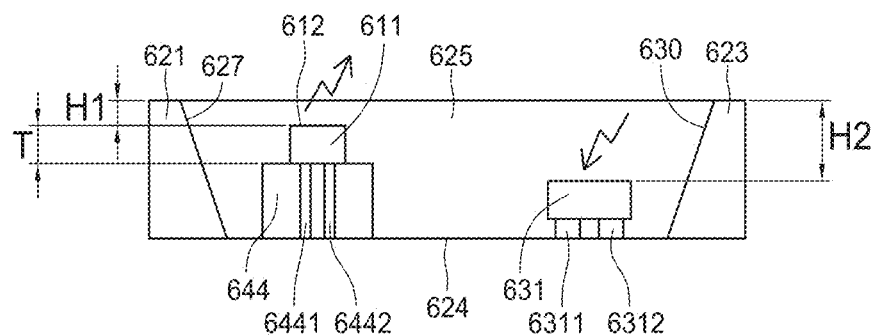
FIG. 6D is a partial cross-sectional view of an optical sensing device in accordance with still another embodiment of the present disclosure.

FIG. 6D discloses a partial cross-sectional view of an optical sensing device in accordance with still another embodiment of the present disclosure. As shown in FIG. 6D, an optical sensing device 604 includes a flip-chip type light-emitting device 611 and a flip-chip type light-receiving device 631. The light-emitting device 611 includes a first electrode and a second electrode (not shown) located under the light-emitting device 611. The light-receiving device 631 includes a first electrode 6311 and a second electrode 6312 located under the light-emitting device 631. There is a connecting device 644 located under the light-emitting device 611 and the width of the connecting device 644 is larger than that of the light-emitting device 611. The connecting device 644 includes two conductive through holes 6441 and 6442 electrically connecting to the first electrode and the second electrode of the light-emitting device 611 respectively. The light-emitting device 611 has a light-emitting surface 612, and there is a distance H1 between the light-emitting surface 612 and the topmost surface of the carrier body 620. The light-receiving device 631 has a light-receiving surface 632, and there is a distance H2 between the light-receiving surface 632 and the topmost surface of the carrier body 620, wherein H1<H2. In one embodiment, the light-emitting device 611 has a height T, and H2>H1+T. The light-emitting device 611, the connecting device 644, and the light-receiving device 631 are in the space 625 which is located between the first block wall 621 and the third block wall 623. The space 625 can be filled in a transparent encapsulating material to protect and to fix the light-emitting device 611, the connecting device 644, and the light-receiving device 631. An inner surface 627 of the first block wall 621 facing the light-emitting device 611 or the light-receiving device 631 is not perpendicular to the lowermost surface 624 of the optical sensing device 604. An inner surface 630 of the third block wall 623 facing the light-emitting device 611 or the light-receiving device 631 is not perpendicular to the lowermost surface 624 of the optical sensing device 604. Therefore, the space 625 where the light-emitting device 611 or the light-receiving device 631 are located has a shape with a wide upper portion and a narrow lower portion from the perspective of the cross-sectional side view. In more detail, the width of the space 625 is getting larger along the direction away from the lowermost surface 624 of the optical sensing device 604. The lower surfaces of the conductive through holes 6441 and 6442, the first electrode 6311, and the second electrode 6312 are exposed to the lowermost surface 624 of the optical sensing device 604. The materials of the block walls can include the light-reflective materials or the light-absorbing materials which reflect light less than the light-reflective material does. The detailed description of the materials of the connecting device 644 and the transparent encapsulating material can be referred to the previous corresponding sections.

Figure 6E:
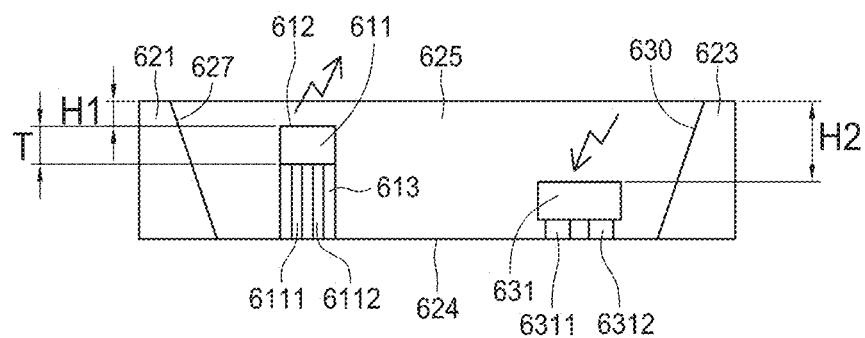
FIG. 6E is a partial cross-sectional view of an optical sensing device in accordance with still another embodiment of the present disclosure.

FIG. 6E discloses a partial cross-sectional view of an optical sensing device in accordance with still another embodiment of the present disclosure. An optical sensing device 605 includes a flip-chip type light-emitting device 611 and a flip-chip type light-receiving device 631. The light-emitting device 611 includes a first electrode 6111 and a second electrode 6112 located under the light-emitting device 611. The first electrode 6111 and the second electrode 6112 are surrounded by a supporting structure 613. Not only surrounds the first electrode 6111 and the second electrode 6112, the supporting structure 613 also covers the lower surface of the light-emitting device 611. The outer surface of the supporting structure 613 is flush with the outer surface of the light-emitting device 611. The lowermost surface of the supporting structure 316 is flush with the lowermost surfaces of the first electrode 6111 and the second electrode 6112. The material of the supporting structure 613 can be a light-reflective material, a light-absorbing material which reflects light less than the light-reflective material does, or a transparent encapsulating material. The light-receiving device 631 includes a first electrode 6311 and a second electrode 6312 located under the light-emitting device 631. The light-emitting device 611 has a light-emitting surface 612, and there is a distance between the light-emitting surface 612 and the topmost surface of the carrier body 620. The light-receiving device 631 has a light-receiving surface 632, and there is a distance H2 between the light-receiving surface 632 and the topmost surface of the carrier body 620, and H1<H2. In one embodiment, the light-emitting device 611 has a height T, and H2>H1+T. The light-emitting device 611 and the light-receiving device 631 are in the space 625 which is located between the first block wall 621 and the third block wall 623. The space 625 can be filled in a transparent encapsulating material to protect and to fix the light-emitting device 611 and the light-receiving device 631. An inner surface 627 of the first block wall 621 facing the light-emitting device 611/the light-receiving device 631 is not perpendicular to the lowermost surface 624 of the optical sensing device 605. An inner surface 630 of the third block wall 623 facing the light-emitting device 611/the light-receiving device 631 is not perpendicular to the lowermost surface 624 of the optical sensing device 605. Therefore, the space 625 where the light-emitting device 611/the light-receiving device 631 are located has a shape with a wide upper portion and a narrow lower portion from the perspective of the cross-sectional side view. In more detail, the width of the space 625 is getting larger along the direction away from the lowermost surface 624 of the optical sensing device 605. The lower surfaces of the first electrode 6111 and the second electrode 6112 of the light-emitting device 611 and the first electrode 6311 and the second electrode 6312 of the light-receiving device 631 are exposed to the lowermost surface 624 of the optical sensing device 605. The materials of the block walls can be included the light-reflective materials or the light-absorbing materials which reflect light less than the light-reflective material does. The detailed description of the material of the transparent encapsulating material can be referred to the previous corresponding section.

Figure 7A:
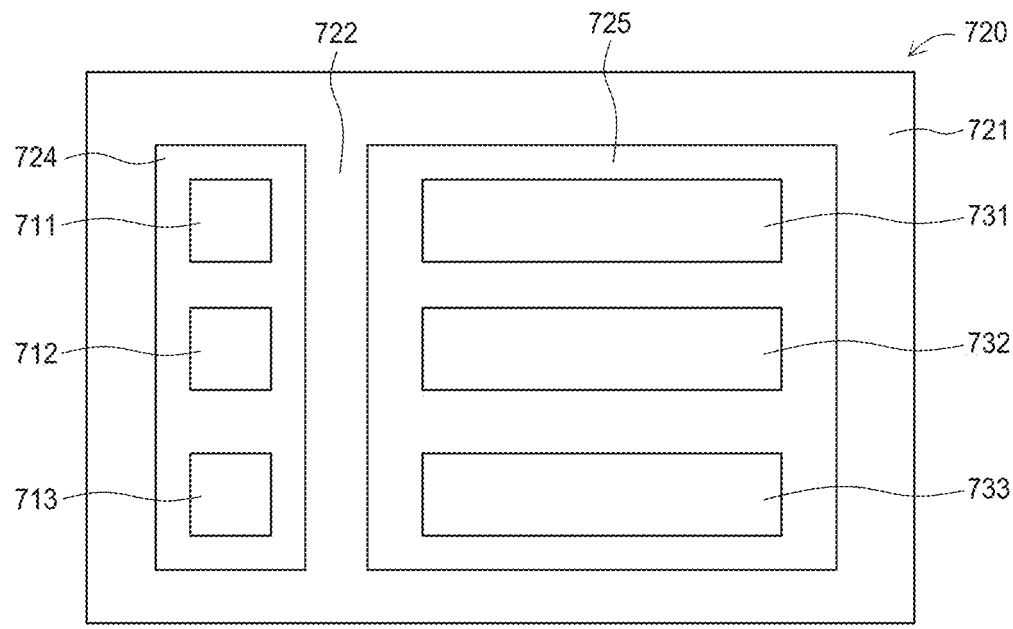
FIG. 7A is a top view of an optical sensing device in accordance with still another embodiment of the present disclosure.

In another embodiment, the optical sensing device includes a plurality of light-emitting devices with different emitting wave bands and a plurality of light-receiving devices with different receiving wave bands. By emitting light with different emitting wave bands to the detected organism, such as the human's skin, one can get variety of physiological signals, such as the heart rhythm, the blood oxygen level, the blood sugar level, and the blood pressure through detecting the returned receiving wave bands. FIG. 7A is a top view of an optical sensing device 701 in accordance with still another embodiment of the present disclosure. the optical sensing device 701 includes a carrier body 720, a first light-receiving device 731, a second light-receiving device 732, a third light-receiving device 733, a first light-emitting device 711, a second light-emitting device 712, and a third light-emitting device 713. The carrier body 720 includes a shell 721 and a block wall 722 to form a first space 724 and a second space 725. The second space 725 is larger than the first space 724. A plurality of light-emitting devices with different emitting wave bands is in the first space 724, and a plurality of light-receiving devices with different receiving wave bands is in the second space 725. The first light-emitting device 711, the second light-emitting device 712, and the third light-emitting device 713 are in the first space 724 while the dominant wavelengths/peak wavelengths of the first light-emitting device 711, the second light-emitting device 712, and the third light-emitting device 713 are different. For example, the wave band is a. green wave band of 500~580 nm, a red wave band of 610~700 nm, and/or an IR wave band of larger than 700 nm. The first light-receiving device 731, the second light-receiving device 732, and the third light-receiving device 733 are located in the second space 725 and the receiving wave bands thereof are respectively corresponding to the dominant wavelengths/peak wavelengths of the first light-emitting device 711, the second light-emitting device 712, and the third light-emitting device 713. The areas of the first light-receiving device 731, the second light-receiving device 732, and the third light-receiving device 733 are larger than those of the first light-emitting device 711, the second light-emitting device 712, and the third light-emitting device 713.

Figure 7B:
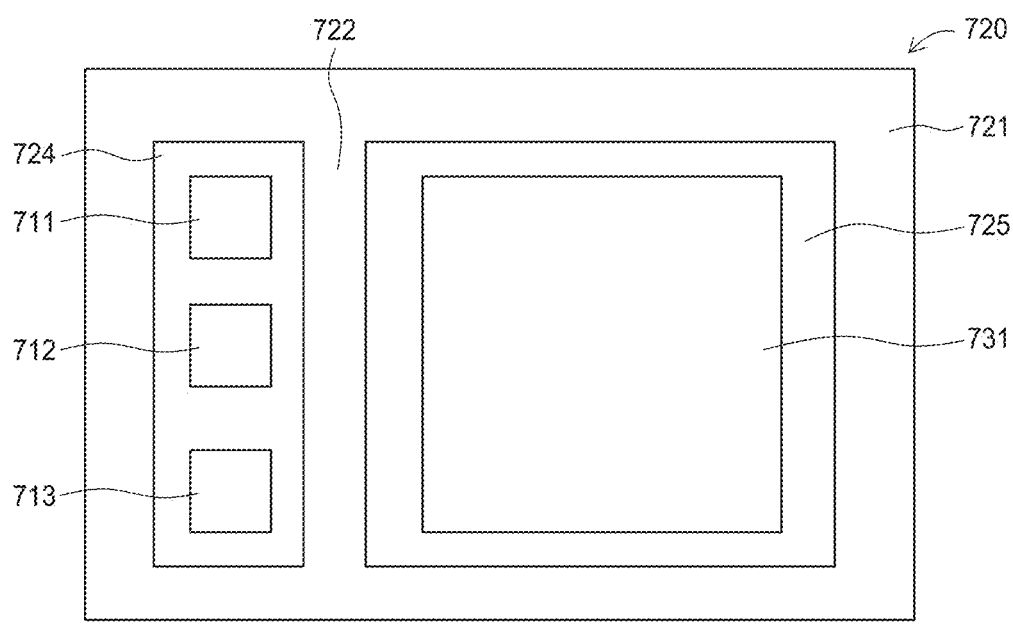
FIG. 7B is a top view of an optical sensing device in accordance with still another embodiment of the present disclosure.

In another embodiment, the optical sensing device includes a plurality of light-emitting devices with different emitting wave bands and a plurality of light-receiving devices with different receiving wave bands. However, the number of the light-receiving devices is smaller than that of the light-emitting devices. In other words, one light-receiving device can receive the lights from different emitting wave bands. As shown in FIG. 7B, an optical sensing device 702 includes a carrier body 720, a first light-receiving device 731, a first light-emitting device 711, a second light-emitting device 712, and a third light-emitting device 713. The carrier body 720 includes a shell 721 and a block wall 722 to form a first space 724 and a second space 725. The second space 725 is larger than the first space 724. A plurality of light-emitting devices with different emitting wave bands is in the first space 724, and a light-receiving device 731 which is less in the number of the light-emitting devices with different receiving wave bands is in the second space 725. The dominant wavelengths/peak wavelengths of the first light-emitting device 711, the second light-emitting device 712, and the third light-emitting device 713 are different. For example, the wave band is a green wave band of 500~580 nm, a red wave band of 610~700 nm, and/or an IR wave band of larger than 700 nm. The receiving wave bands of the first light-receiving device 731 covers the dominant wavelengths/peak wavelengths of the first light-emitting device 711, the second light-emitting device 712, and the third light-emitting device 713. The area of the first light-receiving device 731 is larger than that of the first light-emitting device 711, the second light-emitting device 712, and the third light-emitting device 713.

Figure 8:
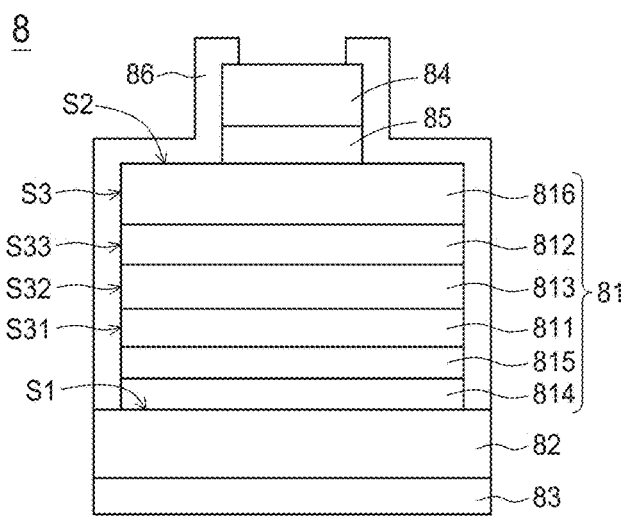
FIG. 8 is a cross-sectional view of a light-receiving device in accordance with one embodiment of the present disclosure.
Figure 9:
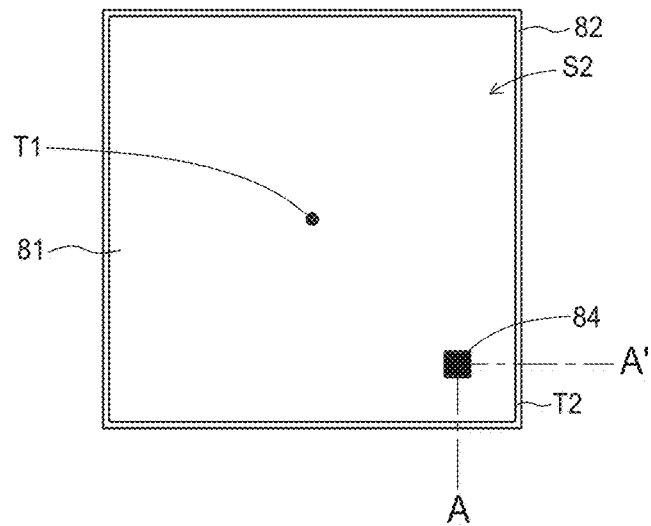
FIG. 9 is a top view of a light-receiving device in accordance with one embodiment of the present disclosure.
Figure 10:
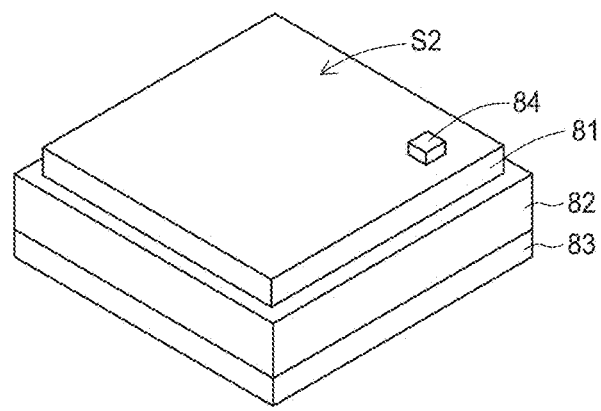
FIG. 10 is a stereoscopic diagram of a light-receiving device in accordance with one embodiment of the present disclosure.

FIG. 8 shows a cross-sectional view of a light-receiving device 8 (photodiode) in accordance with an embodiment of the present disclosure. FIG. 9 shows a top view of FIG. 8 without a protective layer 86. FIG. 10 shows a simplified perspective view of FIG. 8. The light-receiving device 8 includes group III-V semiconductor material and an active region (or a depletion region) for converting light into electrical current or photocurrent, Specifically, the light-receiving device 8 includes a first semiconductor stack 81 and a substrate 82. The substrate 82 is to support the first semiconductor stack 81 and other stacks or structures formed thereon. The first semiconductor stack 81 is formed on the substrate 82 and includes a first-type semiconductor structure 811, a second-type semiconductor structure 812, and an active region 813 located between the first-type semiconductor structure 811 and the second-type semiconductor structure 812. The first-type and the second-type semiconductors have different types. The p-type semiconductor has holes as the majority carriers and n-type semiconductor has the electrons as the majority carriers. For instance, the first-type semiconductor structure 811 is the p-type and the second-type semiconductor structure 811 is n-type and vice versa.

The active region 813 is the region of the light-receiving device 8 to absorb light. The wavelength of the light to be absorbed is determined by the material (or the band gap) of the active region 813. In other words, the active region 813 can absorb a light with a photo energy larger than its band gap. The band gap of the active region 813 can be of 0.72 ev~1.77 ev (corresponding to infrared light with a wavelength between 700 nm and 1700 nm), of 1.77 ev~2.03 ev (corresponding to red light with a wavelength between 610 nm and 700 nm), of 2.1 ev~2.175 ev (corresponding to yellow light with a wavelength between 570 nm and 590 nm), of 2.137 ev~2.48 ev (corresponding to green light with a wavelength between 500 nm and 580 nm), of 2.53 ev~3.1 ev (corresponding to blue or dark blue light with a wavelength between 400 nm and 490 nm), or of 3.1 ev~4.96 ev (corresponding to ultraviolet with a wavelength between 250 nm and 400 nm). In this embodiment, the active region 813 is a semiconductor layer including dopant and the concentration of the dopant is smaller than that of the first-type semiconductor structure 811 or/and the second-type semiconductor 812. Specifically, the concentration of the dopant in the active region 813 is lower than $5 \times 10^{16}$ cm$^{-3}$, such as between $1 \times 10^{15}$ cm$^{-3}$~$5 \times 10^{16}$ cm$^{-3}$. In this embodiment, the dopants in the active region 813 and in the first-type semiconductor structure 811 have the same type, or the dopant in active region 813 is the same as that in the first-type semiconductor structure 811. In another embodiment, the active region 813 is an unintentional doped semiconductor. In this embodiment, the active region 813 of the light-emitting device 8 is to absorb a green light with the wavelength between 500 nm and 580 nm. In this embodiment, the active region 813 is a single layer between the first-type semiconductor structure 811 and the second-type semiconductor structure 812. In other embodiment, the first-type semiconductor structure 811 directly contacts the second-type semiconductor structure 812, and the active region 813 is the interface between the first-type semiconductor structure 811 and the second-type semiconductor structure 812.

The light-emitting device 8 also includes a first electrode pad 83 and a second electrode pad 84 which are electricity connecting to the first semiconductor stack 81 for conducting photocurrent generated by absorption within the first semiconductor stack 81. The first electrode pad 83 and the second electrode pad 84 are located on opposite sides of the first semiconductor stack 81, respectively, so the light-emitting device 8 is viewed as a vertical type. Specifically, the first semiconductor stack 81 has a first surface S1 connecting to substrate 82, a second surface S2 opposite to first surface S1 and away from the substrate 82, and a side surface S3 connecting the first surface S1 and the second surface S2. The first electrode pad 83 locates on the substrate 82, and the second electrode pad 84 locates on the second surface S2.

In this embodiment, since the light-receiving device 8 is a vertical type, the substrate 82 is a conductive material and includes metal, semiconductor or transparent conductive material. The metal includes Cu, Al, Cr, Sn, Au, Ni, Ti, Pt, Pb, Zn, Cd, Sb, Co or alloy thereof. The semiconductor includes group IV semiconductor or group III-V semiconductor, such as Si, Ge, SiC, GaN, GaP, GaAs, AsGaP or InP. The transparent conductive material includes oxide, diamond like carbon (DLC) or Graphene. The oxide is ITO, InO, SnO, CTO, ATO, AZO, ZTO, GZO, IWO, ZnO or IZO. In another embodiment, when the light-emitting device 8 is a non-vertical type, the substrate 8 can include an insulating material, such as sapphire, glass, nitride or oxide, such as $Al_2O_3$ or AlN. Moreover, the substrate 82 can be transparent or non-transparent. The first semiconductor stack 81 can be grown on the substrate 82 or a growth substrate by the epitaxial growth method including metal organic chemical vapor deposition (MOCVD), molecular beam epitaxy (MBE), or hydride vapor deposition (HYPE). When the first semiconductor stack 81 is grown on the growth substrate, the first semiconductor stack 81 is transferred to the substrate 82 by an adhesive layer (not shown) through substrate transfer technique, and the growth substrate can be optionally removed. The substrate 82 can have a dopant or without a dopant. The substrate 82 can be n-type or p-type. In this embodiment, the substrate 82 is p-type GaAs.

As shown in FIG. 9 and FIG. 10, the second surface S2 is a main absorption area of the light-emitting device 8. In order to avoid the second electrode pad 84 from covering too much of the second electrode surface S2 which results in reducing the absorption area and photoelectric conversion efficiency, in a top view of the light-emitting device 8, an area of the second electrode pad 84 is not larger than 15% of the area of the second surface S2, preferably not larger than 10% of the area of the second surface S2, more preferably, not larger than 5% of the area of the second surface S2. Moreover, the area of the second electrode pad 84 is larger than 0.08% of the area of the second surface S2 for facilitating subsequent wire bonding. Specifically, in an embodiment, the area of the second electrode pad 84 is 0.08%~5% of the area of the second surface S2. In this embodiment, the area of the second electrode pad 84 is 0.3%~0.5% of the area of the second surface S2. In another embodiment, a diameter or the longest side of the second electrode pad 84 is not lower than 30 μm. Moreover, the second electrode pad 84 is disposed away from the geometric center T1 of the second surface S2 and adjacent to a peripheral T2 of the first semiconductor stack 81. In this embodiment, there is merely the second electrode pad 84 on the second surface S2 and no other conductive material (extended electrode) is formed on the second surface S2. In another embodiment, besides the second electrode pad 84, an extended electrode is provided to connect to the second electrode pad 84. In a top view, the sum of the area of the extended electrode and the second electrode pad 84 is not larger than 15% of the area of the second surface S2 and larger than 0.08% of area of second surface S2.

As shown in FIG. 8, the light-receiving device 8 further include a protective layer 86 enclosing the first semiconductor stack 81. Specifically, the protective layer 86 covers the second surface S2 and the side surface S3 for preventing moisture or corrosive substance from entering into the first semiconductor stack 81 which adversely affects its electrical property or reliability. In this embodiment, the protective layer 86 directly contacts the second surface S2 and the side surface S3. Specifically, the protective layer 86 directly contacts a sidewall S31 of the first-type semiconductor structure 811, a sidewall S32 of the active region 813 and a sidewall S33 of the second-type semiconductor structure 812 for improving the protection of the first semiconductor stack 81. The protective layer 86 is a single layer and has a reflectivity smaller than 20% in a wavelength of 400 nm~1000 nm. The protective layer 86 can also be used as an anti-reflective layer for decreasing the reflection of incident light when entering into the first semiconductor stack 81. The protective layer 86 includes oxide or nitride, such as SiO2, $Al_2O_3$ or SiN. The protective layer 86 has a refractive index lower than that of the first semiconductor stack 81 for reducing the reflection probability at the second surface S2 and the side surface S3. The protective layer has the refractive index of 1-4~2.1 and is SiN with a thickness of 300 Å~1000 Å. In one embodiment, for improving the anti-reflection, the thickness of the protective layer 86 is an integral multiple of quarter wavelength and the active region 813 has the largest external quantum efficiency (EQE) at that wavelength. In other embodiment, the light-receiving device 8 can optionally be devoid of the protective layer 86 and an encapsulation (not shown) is provided to cover the light-receiving device 8 for preventing moisture or corrosive substance from entering into the first semiconductor stack 81. In one embodiment, the protective layer 86 is a multi-layer and a difference of the refractive index of two adjacent ones in the multilayer is less than 0.7. For example, the protective layer 86 includes a first layer of $SiO_2$ and a second layer of SiN adjacent to the first layer.

In this embodiment, the first semiconductor stack 81 of the light-receiving device 8 further includes a buffer layer 814 and a first barrier layer 815 which are located between the first-type semiconductor structure 811 and the substrate 82. The buffer layer 814 is used to improve the epitaxial quality of the first-type semiconductor structure 811 and other layers formed thereon. The first barrier layer 815 has a band gap higher than that of the first-type semiconductor structure 811 for preventing carrier recombination at the interface between the first-type semiconductor structure 811 and the first barrier layer 815 so photocurrent of the light-receiving device 8 can be enhanced. Each of the buffer layer 814 and the first barrier layer 815 has a dopant so they have the same type as the first-type semiconductor structure 811. The concentration of the dopants in the buffer layer 814 and the first barrier layer 815 are larger than that in the first-type semiconductor structure 811, such as larger than $1 \times 10^{17}$ $cm^{-3}$. Moreover, the first semiconductor stack 81 further includes a second barrier layer 816 located on the second-type semiconductor structure 812. The second barrier layer 816 has a band gap larger than that of the second-type semiconductor structure 812 for preventing carrier recombination at the interface of the second barrier layer 816 and the second-type semiconductor structure 812 so photocurrent of the light-receiving device 8 can be enhanced. The second barrier layer 816 has a dopant to have the same type as the second semiconductor stucture 812. The buffer layer 814 is InGaP, the first barrier 815 is AlGaInP, and the second barrier 816 is AlInP.

The light-receiving device 8 further includes a contact layer 85 located between the first semiconductor stack 81 and the second electrode pad 84. The contact layer 85 is made of a conductive material, According to the material of the first semiconductor stack 81, the material the contact layer 85 can be determined to have a better electrical contact (that is, ohmic contact) with the first semiconductor stack 81 and a lower contact resistance. For example, the material of the contact layer 85 can be group III-V semiconductor, such as GaAs or GaP. In this embodiment, the contact layer 85 has a dopant with a concentration larger than that of second-type semiconductor structure 812. The contact layer 85 is located at a position corresponding to the second electrode pad 84 for preventing the second surface S2 (the main absorption surface) from being covered thereby, so photoelectric conversion efficiency can be enhanced.

In this embodiment, the first-type semiconductor structure 811, the second-type semiconductor structure 812 and the active region 813 include group III-V semiconductor. The group III-V semiconductor includes AlGaInAs series, AlGaInP series, AllnGaN series, AlAsSb series, InGaAsP series, InGaAsN series, or AlGaAsP series, such as AlGaInP, GaAs, InGaAs, AlGaAs, GaAsP, GaP, InGaP, AlInP, GaN, InGaN, AlGaN. In the embodiments, if not specifically mention, the above-mentioned chemical formulas include "stoichiometric compounds" and "non-stoichiometric compounds". A "stoichiometric compound" is, for example, a compound in which the total number of atoms of group III elements is the same as the total number of atoms of group V elements. On the contrary, a "non-stoichiometric compound" is, for example, a compound in which the total number of atoms of group III elements is different from the total number of atoms of group V elements. For example, a compound having a chemical formula of AlGaAs represents that the compound includes Al and/or Ga and/or In as group III elements, and As a group V element, wherein the total number of atoms of the group III elements (Al and/or Ga and/or In) and the total number of atoms of the group V elements (As) may be the same or different. In addition, if the above-mentioned compounds represented by the chemical formulas are stoichiometric compounds, then AlGaInAs series represents for $(Al_{y1}Ga_{(1-y1)})_{1-x1}In_{x1}As$, wherein $0 \le x1$, $0 \le y1 \le 1$; AlGaInP series represents for $(Al_{y2}Ga_{(1-y2)})_{1-x2}In_{x2}P$, wherein $0 \le x2 \le 1$, $0 \le y2 \le 1$; AllnGaN series represents for $(Al_{y3}Ga_{(1-y3)})_{1-x3}In_{x3}N$, wherein $0 \le x3 \le 1$, $0 \le y3 \le 1$; AlAsSb series represents for $AlAs_{x4}Sb_{(1-x4)}$, wherein $0 \le x4 \le 1$; InGaAsP series represents for $In_{x5}Ga_{1-x5}As_{1-y4}P_{y4}$, wherein $0 \le x5 \le 1$, $0 \le y4 \le 1$; InGaAsN series represents for $In_{x6}Ga_{1-x6}As_{1-y5}N_y$, wherein $0 \le x6 \le 1$, $0 \le y5 \le 1$; AlGaAsP series represents for $Al_{x7}Ga_{1-x7}As_{1-y6}P_{y6}$, wherein $0 \le x7 \le 1$, $0 \le y6 \le 1$; InGaPSb series represents for $In_{x8}Ga_{1-x8}P_{y7}Sb_{1-y7}$, wherein $0 \le x8 \le 1$, $0 \le y7 \le 1$. In this embodiment, the first-type semiconductor structure 811, the second-type semiconductor structure 812 and the active region 813 is $In_zGa_{(1-z)}P$, wherein $0<z<1$. In another embodiment, the first-type semiconductor 811 is AlGaInAs: Zn series, AlGaInP:Zn series, or InGaPSb:Zn series. The material of the second-type semiconductor structure 812 is AlGaInAs:Si series, AlGaInP:Si series, or InGaPSb:Si series. The material of the active region 813 is i-AiGaInAs series, i-AlGaInP series, or i-InGaPSb series.

The first electrode pad 83 and the second electrode pad 84 can have the same or different material. In one embodiment, the first electrode pad 83 and the second electrode pad 84 include a metal or a transparent conductive material. The metal can include Cu, Al, Cr, Sn, Au, Ni, Ti, Pt, Pb, Zn, Cd, Sb, Co or alloy thereof. The transparent conductive material can include ITO, InO, SnO, CTO, ATO, AZO, ZTO, GZO, IWO, ZnO, IZO, AlGaAs, GaN, GaP, GaAs, GaAsP, diamond-like carbon (DLC), or graphene.

Figure 11:
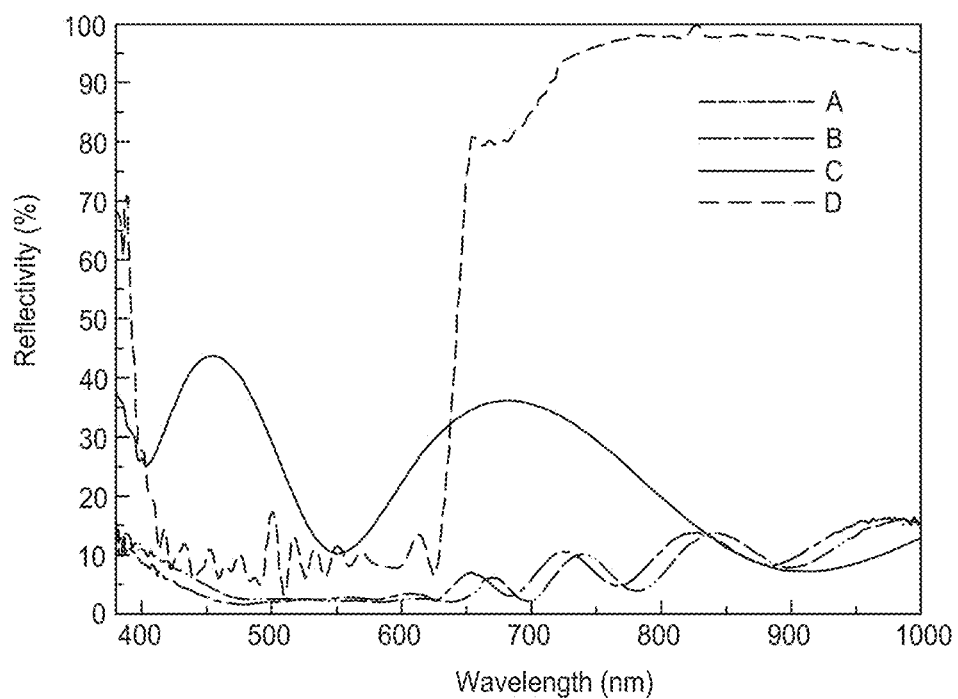
FIG. 11 is a relation diagram of the wavelength and the reflectivity of the implementation groups of the light-receiving devices in accordance with the embodiments of the present disclosure and the control groups of other light-receiving devices.

FIG. 11 shows the relation between wavelength and reflectivity of the light-emitting device of the experimental examples and the comparative examples. Lines A and B represent the relation between wavelength and reflectivity of the light-receiving device of the first and second experimental examples, respectively. The light-receiving devices of the first and second experimental examples have the similar structure (as shown in FIG. 8) and both of the first semiconductor stacks 81 are group II-V semiconductor. The difference is that the active region 813 of the first semiconductor layer 81 of the first experimental example is $In_{0.51}Ga_{0.49}P$ and the active region 813 of the first semiconductor layer 81 of the second experimental example is $(Al_{0.1}Ga_{0.9})_{0.5}In_{0.5}P$. Lines C and D represent the relation between wavelength and reflectivity of the light-receiving device of the first and second comparative examples, respectively. The light-receiving devices of the first and second comparative examples are group IV semiconductor as the semiconductor stack, such as Si.

Figure 12A:
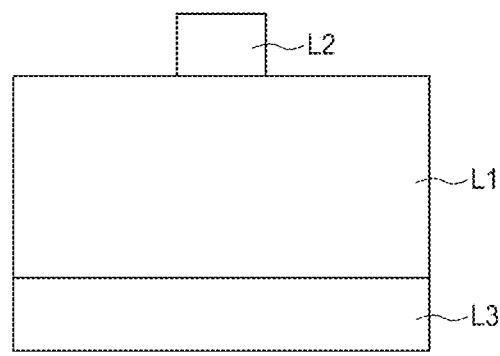
FIG. 12A is a cross-sectional view of a light-receiving device of the first control group.
Figure 12B:
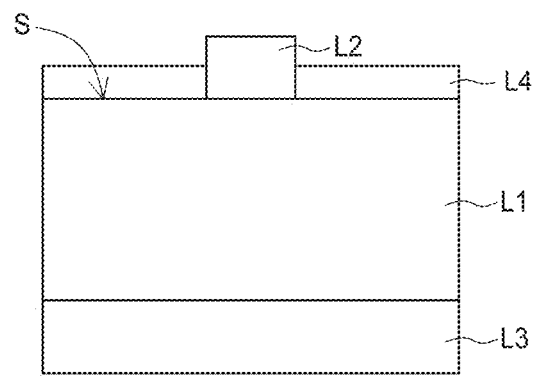
FIG. 12B is a cross-sectional view of a light-receiving device of the second control group.

FIGS. 12A and 12B are cross-sectional views of the light-receiving devices of the first and second comparative examples, and they are merely illustrative and can include other elements. The light-receiving device of the first comparative example include a Si semiconductor layer L1, a first electrode pad L2, and a second electrode pad L3. The first electrode pad L2, and a second electrode pad L3 are disposed on opposite sides of the Si semiconductor layer L1. The light-receiving device of the second comparative example has a similar structure to that of the first comparative example, except that the light-receiving device of the second comparative example further has a distributed Bragg reflector L4 on the main absorption surface S. The distributed Bragg reflector includes first layers and second layers which are alternately stacked on each other. The first layer has a refractive index different from that of the second layer and a difference therebetween is over 0.8 for achieving a good filter effect. For example, the first layer and the second layer are $SiO_2$ and $TiO_2$, respectively. In FIG. 11, the graph is measured by an instrument produced by Hitachi (U-4100).

As shown in FIG. 11, in the first and second experimental examples (A, B), the light-receiving devices have a reflectivity smaller that 20% in the wavelength of 400 nm~800 nm. As shown in FIG. 11, in the first and second comparative examples (C, D), the light-receiving devices have a larger reflectivity in the wavelength of 400 nm~800 nm, in line C, the reflectivity at 450 nm is of 44% and the reflectivity at 680 nm is of 37%. In line D, the light-receiving device has a reflectivity larger than 80% in the wavelength of 650 nm~1000 nm. In addition, for the light-receiving devices of the first and second experimental examples, there are nearly no oscillation in the receiving wave band which is the green range (500 nm~580 nm). In the light-receiving device of the second comparative example (D), the oscillation in the aforesaid receiving wave band is about 15~20 nm which results from the distributed Bragg reflector. The oscillation is defined as a wavelength difference between two adjacent wave peaks or between two adjacent wave valleys within the receiving wave band.

Figure 13:
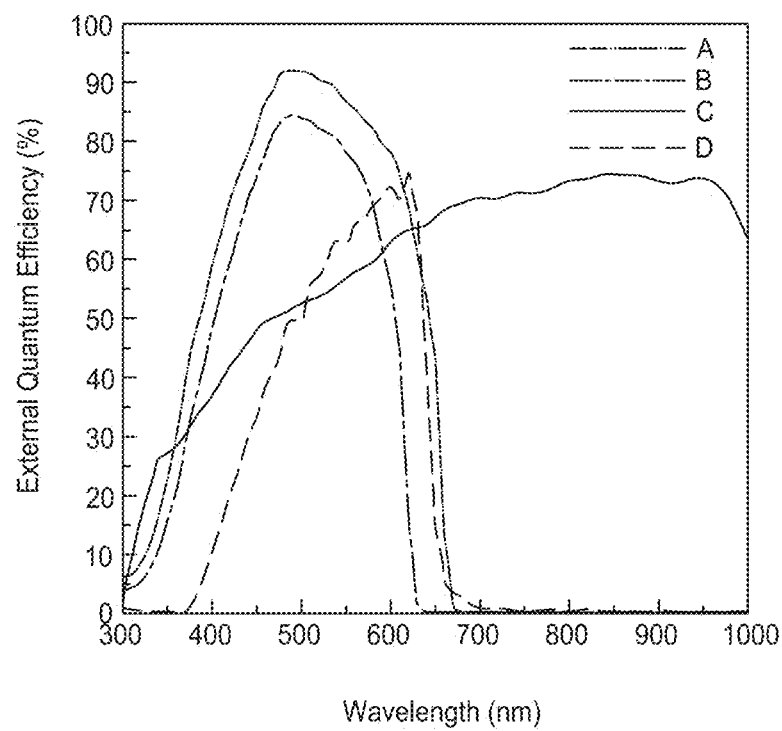
FIG. 13 is a relation graph of the wavelength and the external quantum efficiency (EQE) of light-receiving devices in the implementation groups in accordance with the embodiments of the present disclosure and the control groups of other light-receiving devices.

FIG. 13 shows the relation between wavelength and EQE of the light-emitting devices of the first and second experimental examples (A, B) and the first and second comparative examples (C, D). In line A, the light-emitting device of the first experimental example has the largest EQE of 92% at 475 nm. In line B, the light-emitting device of the second experimental example has the largest EQE of 85% at 477 nm. In line C, the light-emitting device of the first comparative example has the largest EQE of 74% at 840 nm. In line D, the light-emitting device of the second comparative example has the largest EQE of 75% at 620 nm.

In line C, the light-receiving device of the first comparative example includes group IV semiconductor stack without distributed Bragg reflector (see FIG. 12A), and has the EQE of 53~70% at 500~700 nm and the EQE larger than 60% at 700~1000 nm. In line D, the light-receiving device of the second comparative example includes group IV semiconductor stack with distributed Bragg reflector on the main absorption surface S. The distributed Bragg reflector is designed to reflect a light with a wavelength of 700~100 nm to filter the non-receiving wave band (the detail of the non-receiving wave band will be described later) so most of light with the wavelength of 700~1000 nm does not enter into the light-receiving device of the second comparative example to produce electrical signal. The light-receiving device of the second comparative example has the EQE of 52~75% at 500~680 nm and the EQE smaller than 40% at 700~1000 nm. On the contrary, in the first and second experimental examples, the light-receiving devices have the EQE larger than 70%, preferably larger than 78% and more preferably larger than 83% at 500~580 nm. The light-receiving device of the first experimental example has the EQE larger than 90% at 500~680 nm, even larger than 93%. In absence of distributed Bragg reflector, the light-receiving devices of the first and second experimental examples have the EQE smaller than 10%, preferably smaller than 3% at 700~1000 nm. Although the light-receiving devices of the first and second experimental examples and the first and second comparative examples have the EQE larger than 40% in the receiving wave band which is the green range (500 nm~580 nm), when having an infrared light with a wavelength of 700~800 nm in the environment, the light-receiving devices of the first and second experimental examples have less interference than those of the first and second comparative example so the detecting accuracy is enhanced. Moreover, the light-receiving devices of the first and second experimental examples have a higher signal-to-noise ratio (S/N) than those of the first and second comparative examples. The definition of the S/N will be described later. Compared to the second comparative example, during the process of making the light-receiving devices of the first and second experimental examples, it does not have a step to form the distributed Bragg reflector, thereby reducing the process step and cost. In other words, the light-receiving devices of the first and second experimental examples have higher conversion efficiency than those of the first and second comparative examples within the receiving wave band, and thus when the signal within the receiving wave band to be detected is weaker, the light-receiving devices of the first and second experimental examples can still work and produce the photocurrent in response to the signal. In addition, since the light-receiving devices of the first and second experimental examples have low EQE at the non-receiving wave band, they will not be interfered with the red light or infrared light having a wavelength larger than 700 nm so the light-receiving devices of the first and second experimental examples have a good S/N for increasing the detecting accuracy. In FIG. 13, the graph is measured by an instrument produced by OPRO-SOLAR (SR300).

The S/N is obtained by dividing an integral area of a selected wavelength range within the receiving wave band by an integral area of a selected wavelength range within the non-receiving wave band. For example, the selected wavelength within the receiving wave band is the green range of 500 nm~550 nm and the selected wavelength within the non-receiving wave band is of 600 nm~700 nm which is larger than the receiving wave band. The S/N is calculated based on the following formula I:

$$S/N \text{ ratio} = \frac{\int_{500}^{550} EQE \times \left(\frac{1}{\lambda}\right) d\lambda}{\int_{600}^{700} EQE \times \left(\frac{1}{\lambda}\right) d\lambda} \quad \text{formula I}$$

Referring to FIG. 13, when the receiving wave band is within the green range, the light-receiving devices of the first and second experimental examples and the second comparative example (A, B, and D) have lower EQE within the non-receiving wave band. Based on the definition mentioned above, the light-receiving devices of the first and second experimental examples have a larger S/N than that of the light-receiving devices of the second comparative example. The S/N of the first and second experimental examples is larger than 1.4, preferably larger than 1.6. The S/N of the second comparative example is not over 1.2. Specifically, the S/N of the first experimental example is 1.63, the S/N of the second experimental example is 4.8 and the S/N of the second comparative example is 1.15.

Referring to FIG. 13, when the receiving wave band is within the green range, the light-receiving device of the first comparative example (line C) devoid of the distributed Bragg reflector on a top surface has the EQE at the receiving wave band smaller than that at the non-receiving wave band. Referring to the light-receiving device of the second comparative example (line D), due to the distributed Bragg reflector on the top surface, less of the light with a wavelength within the non-receiving wave band is absorbed and converted into electrical signal so the EQE at the receiving wave band is far larger than that at the non-receiving wave band and the difference therebetween 40% and 75%. In the first and second experimental examples, since the light-receiving devices does not have the distributed Bragg reflector and has a relatively low EQE at the non-receiving wave band, when light within the receiving wave band and the non-receiving wave band enters into the light-receiving devices, a difference between the EQE at the receiving wave band and the EQE at the non-receiving wave band is ≥75%, preferably ≥80%, more preferably 85%.

Referring to line A of FIG. 13, the light-receiving device of the first experimental example has a wavelength ($W_{A0}$) within the receiving wave band at which the EQE is largest and a wavelength ($W_{A1}$) within the non-receiving wave band larger than the receiving wave band. The EQE decreases to 2% at the wavelength ($W_{A1}$). A distance between $W_{A1}$ and $W_{A0}$ is $W_A$; $W_{A1} \geq W_{A0}$, 0 nm<$W_A$(=$W_{A1}-W_{A0}$)≥250 nm, preferably 0 nm<$W_A$≤220 nm. For example, $W_{A0}$ is about 500 nm, $W_{A1}$ is about 680 nm and $W_A$ is about 180 nm. Referring to line B, in the second experimental example, a difference between a wavelength ($W_{B0}$) within the receiving wave band at which the EQE is largest and a wavelength ($W_{B1}$) within the non-receiving wave band at which the EQE decreases to 2% is $W_B$, wherein $W_{B1} \leq W_B$, 0 nm<$W_B$ (=$W_{B1}-W_{B0}$)≤200 nm, preferably 0 nm<$W_B$≤180 nm. For example, $W_{B0}$ is about 500 nm. $W_{B1}$ is about 630 nm and $W_B$ is about 130 nm.

The light-receiving devices of the first and second experimental examples have the main absorption surface with an area. $M_A(mm^2) \leq 6.5$, preferably $M_A(mm^2) \leq 5$, more preferably $M_A(mm^2) \leq 4$, such as 3 $mm^2$, 2.25 $mm^2$, 1 $mm^2$. In the all wavelength range of FIG. 13, The light-receiving devices of the first and second experimental examples have the largest $EQE_A$ (%) and $EQE_B$ (%), respectively. $EQE_A$ (%) or $EQE_B$ (%)/$M_A(mm^2)$) is ≥13, preferably ≥18, more preferably ≥20 and $EQE_A$ (%) or $EQE_B$ (%)/$M_A(mm^2)$)≤95. For example, $EQE_A$ (%) or $EQE_B$ (%) is 92 and $M_A(mm^2)$ is 6.25; $EQE_A$ (%) or $EQE_B$ (%) is 92 and $M_A(mm^2)$ is 4; $EQE_A$ (%) or $EQE_B$ (%) is 92 and $M_A(mm^2)$ is 3; $EQE_A$ (%) or $EQE_B$ (%) is 85 and $M_A(mm^2)$ is 6.25; $EQE_A$ (%) or $EQE_B$ (%) is 85 and $M_A(mm^2)$ is 4; $EQE_A$ (%) or $EQE_B$ (%) is 85 and $M_A(mm^2)$ is 3.

In the receiving wave band which is the green range (500 nm~580 nm) of FIG. 13, the light-receiving devices of the first and second experimental examples have the largest $EQE_C$ and $EQE_D$ (%), respectively. $EQE_C$(%) or $EQE_D$(%)/$M_A(mm^2) \geq 13$, preferably ≥18, more preferably ≥20 and $EQE_C$(%) or $EQE_D$(%)/$M_A(mm^2) \leq 95$. For example, $EQE_C$ (%) or $EQE_D$(%) is 90 and $M_A(mm^2)$ is 6.25; $EQE_C$(%) or $EQE_D$(%) is 90 and $M_A(mm^2)$ is 4; $EQE_C$(%) or $EQE_D$(%) is 90 and $M_A(mm^2)$ is 3; $EQE_C$(%) or $EQE_D$(%) is 84 and $M_A(mm^2)$ is 6.25; $EQE_C$(%) or $EQE_D$(%) is 84 and $M_A(mm^2)$ is 4; is $EQE_C$(%) or $EQE_D$(%) is 84 and $M_A(mm^2)$ is 3.

The light-receiving device of the first comparative example has a main absorption area with the area $M_B(mm^2)$ of about 5 and the largest $EQE_E$(%). The light-receiving device of the second comparative example has a main absorption area with the area $M_C(mm^2)$ of about 9 and the largest $EQE_F$(%). In the all wavelength range of FIG. 13, for the light-receiving device of the first comparative example, a ratio of the largest $EQE_E$(%) to the area $M_B(mm^2)$ is about 14. For the light-receiving device of the second comparative example, a ratio of the largest $EQE_F$(%) to the area $M_C(mm^2)$ is about 8. The ratios ($EQE_E$ (%)/$M_B(mm^2)$ and $EQE_F$ (%)/$M_C(mm^2)$) are lower than that of the light-receiving devices of the first and second experimental examples. In the receiving wave band which is the green range (500 nm~580 nm), the light-receiving devices of the first and second comparative examples have the largest $EQE_G$ (%) and $EQE_H$ (%), respectively. For the light-receiving device of the first comparative example, a ratio of the largest $EQE_G$ (%) to the area $M_C(mm^2)$ is about 11. For the light-receiving device of the second comparative example, a ratio of the largest $EQE_H$ (%) to the area $M_C(mm^2)$ is about 7. The ratios ($EQE_G$ (%)/$M_B(mm^2)$ and $EQE_H$ (%)/$M_C(mm^2)$) are lower than that of the light-receiving devices of the first and second experimental examples.

Referring to lines A and B of FIGS. 11 and 13, the light-receiving devices of the first and second experimental examples have the reflectivity smaller than 5% in the wavelength of 530 nm, such as 2.47% and 2.36%, respectively. The light-receiving devices of the first and second comparative examples have the reflectivity larger than 9% in the wavelength of 530 nm, such as 14.13% and 9.74%, respectively. In addition, the light-receiving devices of the first and second experimental examples have the EQE larger than 80% at 530 nm, such as 89.88% and 81.42%, respectively. The light-receiving devices of the first and second comparative examples have the EQE smaller than 65% at 530 nm, such as 55.81% and 59.98%, respectively.

Figure 14A:
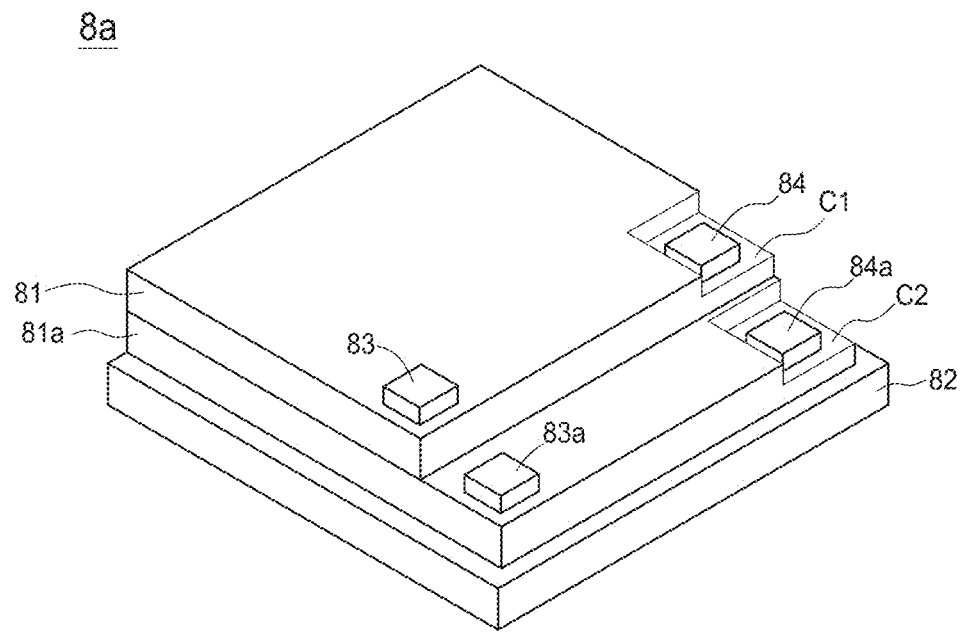
FIG. 14A is a stereoscopic diagram of a light-receiving device in accordance with another embodiment of the present disclosure.
Figure 14B:
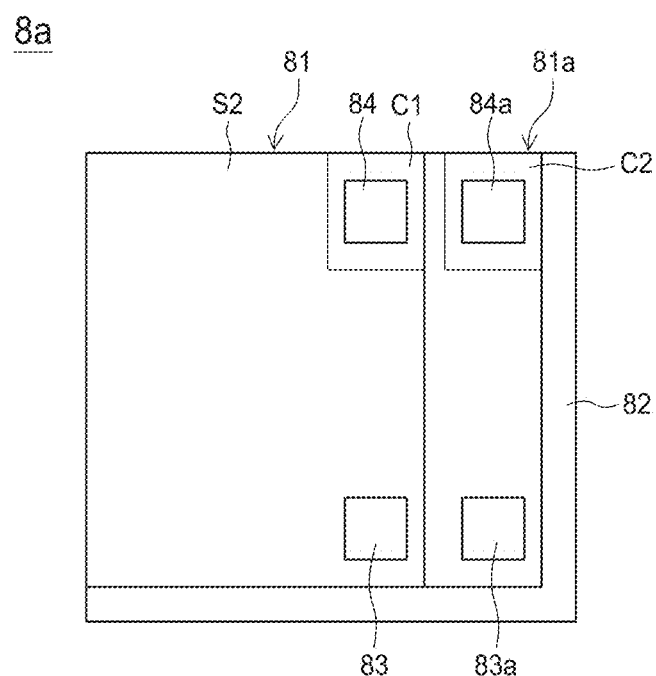
FIG. 14B is a top view of a light-receiving device in accordance with another embodiment of the present disclosure.

FIGS. 14A and 14B are a perspective view and a top view of a light-receiving device in accordance with an embodiment of the present disclosure, respectively. Similar to the previous embodiment, the light-receiving device 8a includes a substrate 82 and a first semiconductor stack 81 formed on the substrate 82. The difference is that the light-receiving device 8a further includes a second semiconductor stack 81a between the first semiconductor stack 81 and the substrate 82. The second semiconductor stack 81a and the first semiconductor stack 81 have group III-V semiconductor as the active region for absorbing light. The second semiconductor stack 81a can have the same structure as the first semiconductor stack 81 and includes the first-type semiconductor structure, the active region and the second-type semiconductor structure. In one embodiment, the second semiconductor stack 81a can have a structure different from the first semiconductor stack 81.

Furthermore, the light-receiving device 8a includes first electrodes 83, 83a and second electrodes 84, 84a. The first electrode pad 83 and the second electrode pad 84 are disposed on a side of the first semiconductor stack 81 away from the substrate 82 for electrically connecting thereto, thereby conducting a first photocurrent generated by absorption of a light with a first wavelength in the first semiconductor stack 81. The first electrode pad 83a and the second electrode pad 84a are disposed on a side of the second semiconductor stack 81a away from the substrate 82 for electrically connecting thereto, thereby conducting a second photocurrent generated by absorption of a light with a second wavelength in the second semiconductor stack 81a. The first semiconductor stack 81 has a recess C1 to expose the first-type semiconductor structure 811 (not shown). The first electrode pad 83 and the second electrode pad 84 are disposed on the second-type semiconductor structure 812 (not shown) and the recess C1, respectively. Likewise, the second semiconductor stack 81 has a recess C2 to expose the first-type semiconductor structure (not shown). The first electrode pad 83a and the second electrode pad 84a are disposed on the second-type semiconductor structure 812 (not shown) and the recess C2, respectively.

As mentioned above, the first wavelength can be equal to, smaller or larger than the second wavelength. In other words, the active region of the second semiconductor stack 81a has a band gap different from that of the first semiconductor stack 81. Preferably, the band gap of the active region of the second semiconductor stack 81a is larger than that of the first semiconductor stack 81. In this embodiment, the band gap of the active region of the first semiconductor stack 81 is 2.138 eV~2.58 eV for absorbing the wavelength of 480 nm~580 nm. The band gap of the active region of the second semiconductor stack 81a is 1.77 eV~2.138 eV for absorbing the wavelength of 580 nm~700 nm. For example, the active region of the first semiconductor stack 81 is InGaP with the band gap of 2.25 eV for absorbing the wavelength of 550 nm and the active region of the second semiconductor stack 81a is InGaAs with the band gap of 1.88 eV for absorbing the wavelength of 660 nm.

In another embodiment, the band gap of the active region of the first semiconductor stack 81 is 1.65 eV~4.13 eV for absorbing the wavelength of 300 nm~750 nm. The band gap of the active region of the second semiconductor stack 81a is 1.21 eV~1.65 eV for absorbing the wavelength of 750 nm~1025 nm. The active region of the first semiconductor stack 81 is AlGaInP series, such as InGaP. The active region of the second semiconductor stack 81a is AlGaAs series or InGaAsP series, such as InGaAs.

Si used as the semiconductor stack in the light-receiving device of the first comparative example has the EQE higher than 40% at a wavelength of 500 nm~1000 nm. Similar to the light-receiving device 8a, the light-receiving device of the first comparative example can be in response to the wavelength of 550 nm and 660 nm and converts them into electrical signals, however, the electrical signals cannot be separated by the two wavelengths. In other words, the aforesaid wavelengths (550 nm and 660 nm) can be absorbed by the light-receiving device of the first comparative example, but it cannot be known what exactly the absorbed wavelength is and what a ratio between the two wavelengths is in the detection environment. Compared to the first comparative example, the light-receiving device 8a of this embodiment can produce concurrently photocurrents in response to the different wavelengths which can be separated thereby so the resolution between two different wavelengths can be improved for applying beneficially in the bio-medical sensing technology.

Figure 14C:
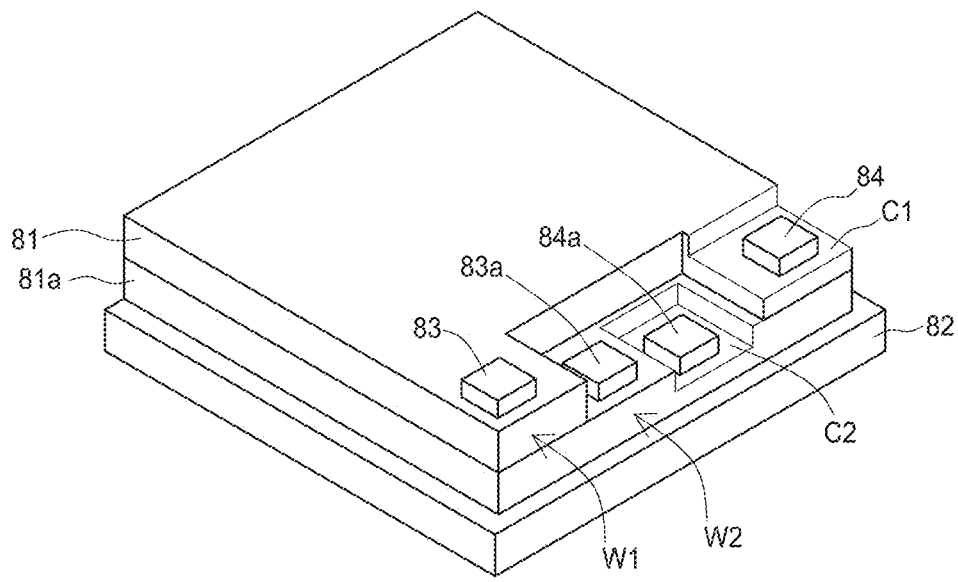
FIG. 14C is a stereoscopic diagram of a light-receiving device in accordance with still another embodiment of the present disclosure.
Figure 14D:
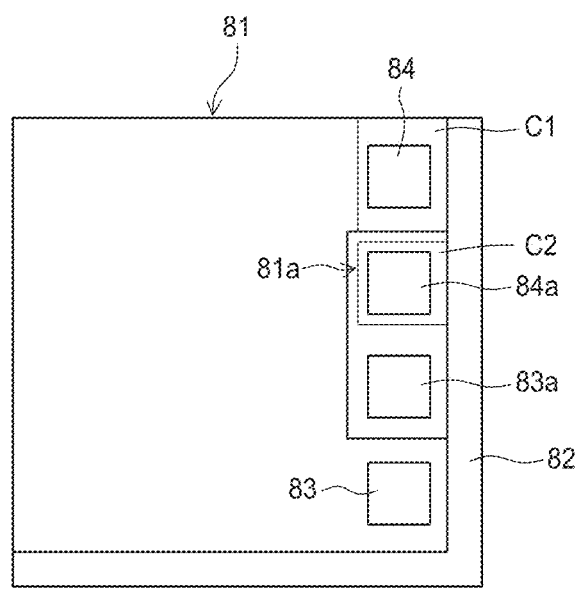
FIG. 14D is a top view of a light-receiving device in accordance with still another embodiment of the present disclosure.

FIGS. 14C and 14D are a perspective view and a top view of a light-receiving device 8b in accordance with an embodiment of the present disclosure, respectively. The light-receiving device 8b has a structure similar to the light-receiving device 8a. The difference is the arrangement of the first electrodes 83, 83a and the second electrodes 84, 84a and the shapes of the first semiconductor stack 81. Specifically, the first semiconductor stack 81 has a sidewall W1 coplanar with a sidewall W2 of the second semiconductor stack 81a such that, in the top view, the first electrode pads 83, 83a and the second electrode pad 84, 84a can be arranged in a line. Therefore, the first semiconductor stack 81 of the light-receiving device 8b has a larger absorption area than that of the light-receiving devices 8a of FIGS. 14A and B for improving the photoelectric conversion efficiency.

Figure 14E:
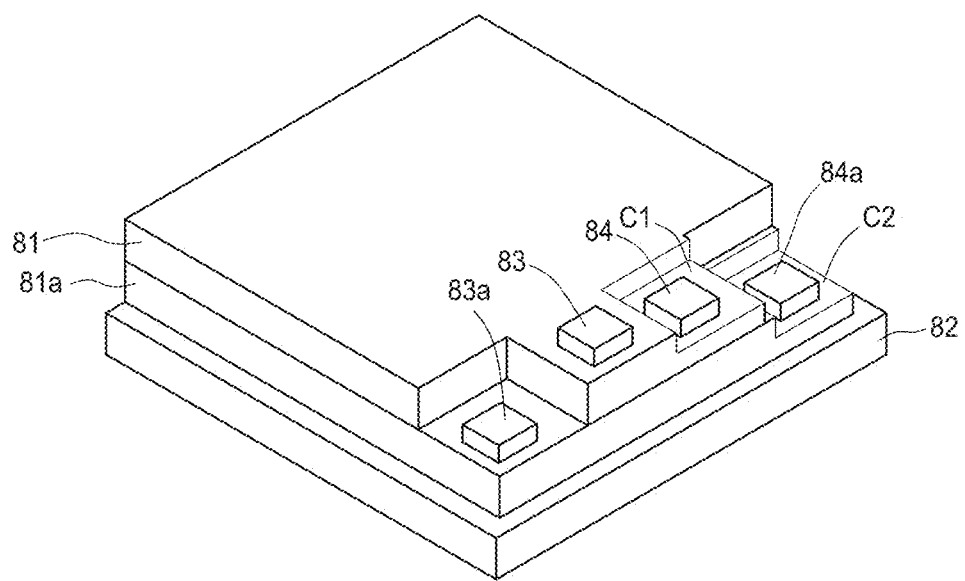
FIG. 14E is a stereoscopic diagram of a light-receiving device in accordance with still another embodiment of the present disclosure.
Figure 14F:
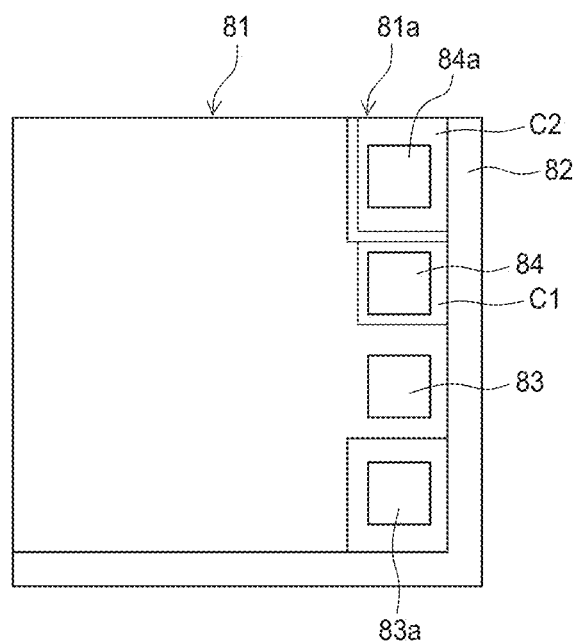
FIG. 14F is a top view of a light-receiving device in accordance with still another embodiment of the present disclosure.

FIGS. 14E and 14F are a perspective view and a top view of a light-receiving device 8c in accordance with an embodiment of the present disclosure, respectively. The light-receiving device 8c has a structure similar to the light-receiving device 8b. The difference is that the first electrode pad 83 and the second electrode pad 84 are disposed between the first electrode pad 83a and the second electrode pad 84a. Similar to the light-receiving device 8b of FIGS. 14C and 14D, the first semiconductor stack 81 of the light-receiving device 8c has a larger absorption area than that of the light-receiving devices 8a of FIG. 14B for improving the photoelectric conversion efficiency.

Figure 15A:
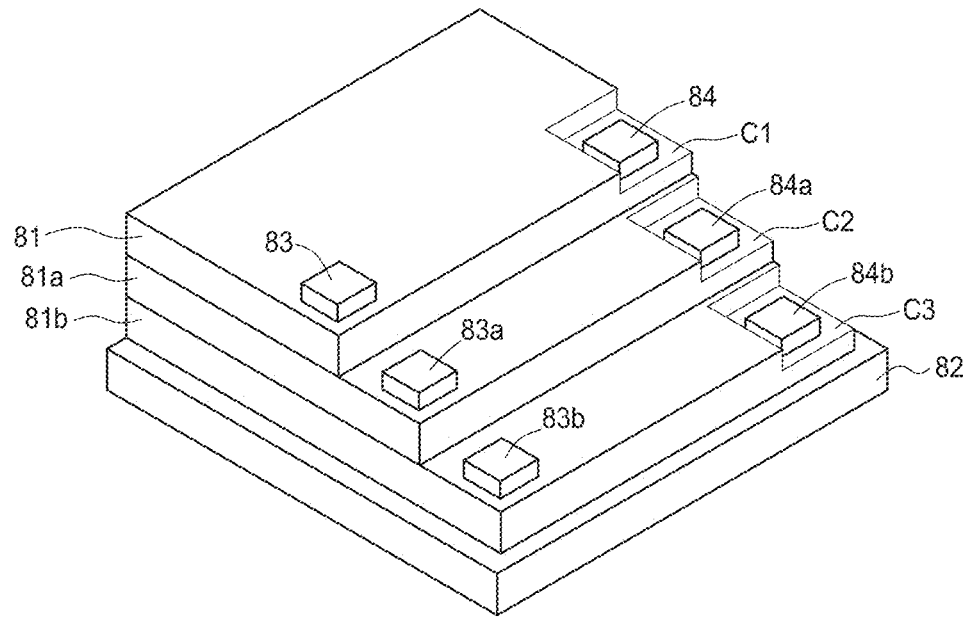
FIG. 15A is a stereoscopic diagram of a light-receiving device in accordance with still another embodiment of the present disclosure.
Figure 15B:
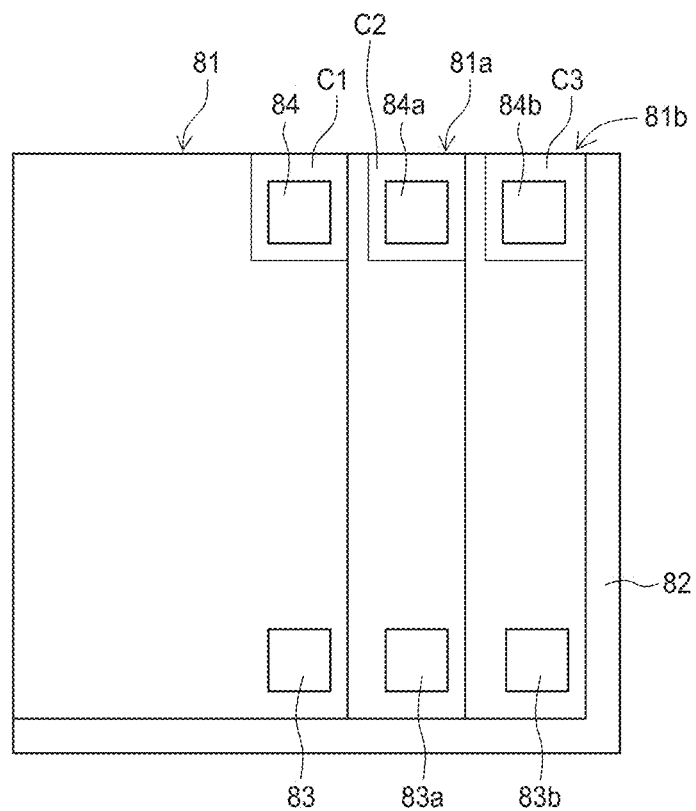
FIG. 15B is a top view of a light-receiving device in accordance with still another embodiment of the present disclosure.

FIGS. 15A and 15B are a perspective view and a top view of a light-receiving device 8d in accordance with an embodiment of the present disclosure, respectively. The light-receiving device 8d has a structure similar to the light-receiving device 8a and includes the substrate 82, the second semiconductor stack 81a and the first semiconductor stack 81. The difference is that the light-receiving device 8d further includes a third semiconductor stack 81b between the second semiconductor stack 81a and the substrate 82. The third semiconductor stack 81b, the second semiconductor stack 81a, and the first semiconductor stack 81 include group III-V semiconductor as the active region for absorbing light. The third semiconductor stack 81b has the same structure as the first semiconductor stack 81 and includes the first-type semiconductor structure, the active region, and the second-type semiconductor structure.

The light-receiving device 8d further includes a first electrode pad 83b disposed on a side of the third semiconductor stack 81b away from the substrate 82 for electrically connecting thereto, thereby conducting a third photocurrent generated by absorption of a light with a third wavelength in the third semiconductor stack 81b. The third semiconductor stack 81b includes a recess C3 to expose the second-type semiconductor structure and the first electrode pad 83b and the second electrode pad 84b are disposed on the first-type semiconductor structure and the recess C3, respectively.

As mentioned above, the third wavelength is equal to, larger, or smaller than the second wavelength and the first wavelength. In other words, the third semiconductor stack 81b has a band gap same as or different from that of the first semiconductor stack 81 and the second semiconductor stack 81a. Preferably, the third semiconductor stack 81b has a band gap smaller that of the second semiconductor stack 81a and the second semiconductor stack 81a has a band gap smaller that of the first semiconductor stack 81. In this embodiment, the first semiconductor stack 81 has a band gap of 2,138 eV~2.58 eV for absorbing a wavelength of 480 nm~580 nm, the second semiconductor stack 81a has a band gap of 1.77 eV~2.138 eV for absorbing a wavelength of 580 nm~700 nm, and the third semiconductor stack 81b has a band gap of 0.73 eV~1.55 eV for absorbing a wavelength of 800 nm~1696 nm. For example, the active region of the first semiconductor stack 81 is InGaP with the band gap of 2.25 eV for absorbing a green light having a wavelength of 550 nm, the active region of the second semiconductor stack 81a is InGaAs with the band gap of 1.88 eV for absorbing a red light having a wavelength of 660 nm, and the active region of the third semiconductor stack 81b is InGaAs with the band gap of 0.95 eV for absorbing an infrared red light having a wavelength of 1300 nm.

The light-receiving device 8b has the first semiconductor stack 81, the second semiconductor stack 81a and the third semiconductor stack 81b with different band gaps for absorbing light with different wavelengths so as to detect multiple wavelengths in the detection environment.

Figure 15C:
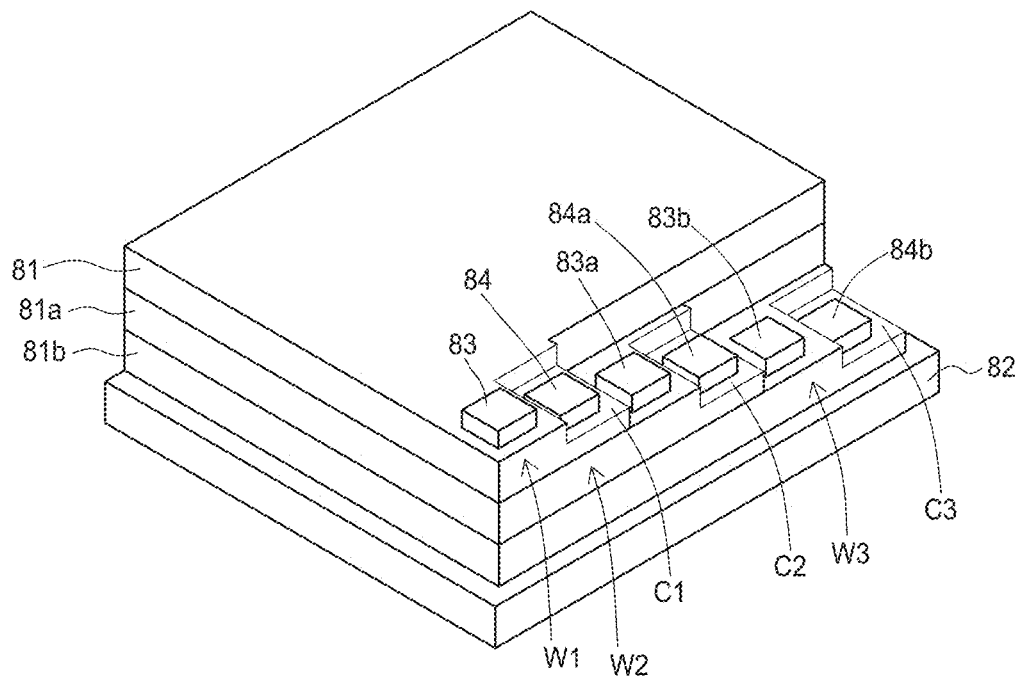
FIG. 15C is a stereoscopic diagram of a light-receiving device in accordance with still another embodiment of the present disclosure.
Figure 15D:
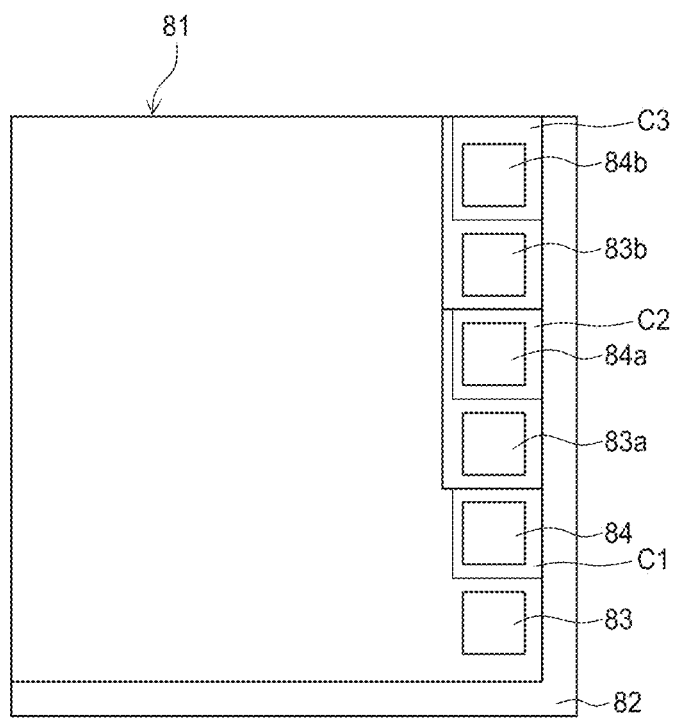
FIG. 15D is a top view of a light-receiving device in accordance with still another embodiment of the present disclosure.

FIGS. 15C and 15D are a perspective view and a top view of a light-receiving device Se in accordance with an embodiment of the present disclosure, respectively. The light-receiving device 8e has a structure similar to the light-receiving device of FIGS. 15A and 15B. The difference is the arrangement of the first electrodes 83, 83a, 83b and the second electrodes 84, 84a, 84b and the shapes of the first semiconductor stack 81 and the second semiconductor stack 81a. Specifically, the first semiconductor stack S1 has a sidewall W1 coplanar with a sidewall W2 of the second semiconductor stack 81a and the second semiconductor stack 81a has a sidewall W2 coplanar with a sidewall W3 of the second semiconductor stack 81a such that, in the top view, the first electrode pads 83, 83a, 83b and the second electrode pad 84, 84a, 84b can be arranged in a line. Therefore, the first semiconductor stack 81 and the second semiconductor stack 81a of the light-receiving device 8e has a larger absorption area than that of the light-receiving devices 8d of FIGS. 15A and 15B for improving the photoelectric conversion efficiency.

Figure 16:
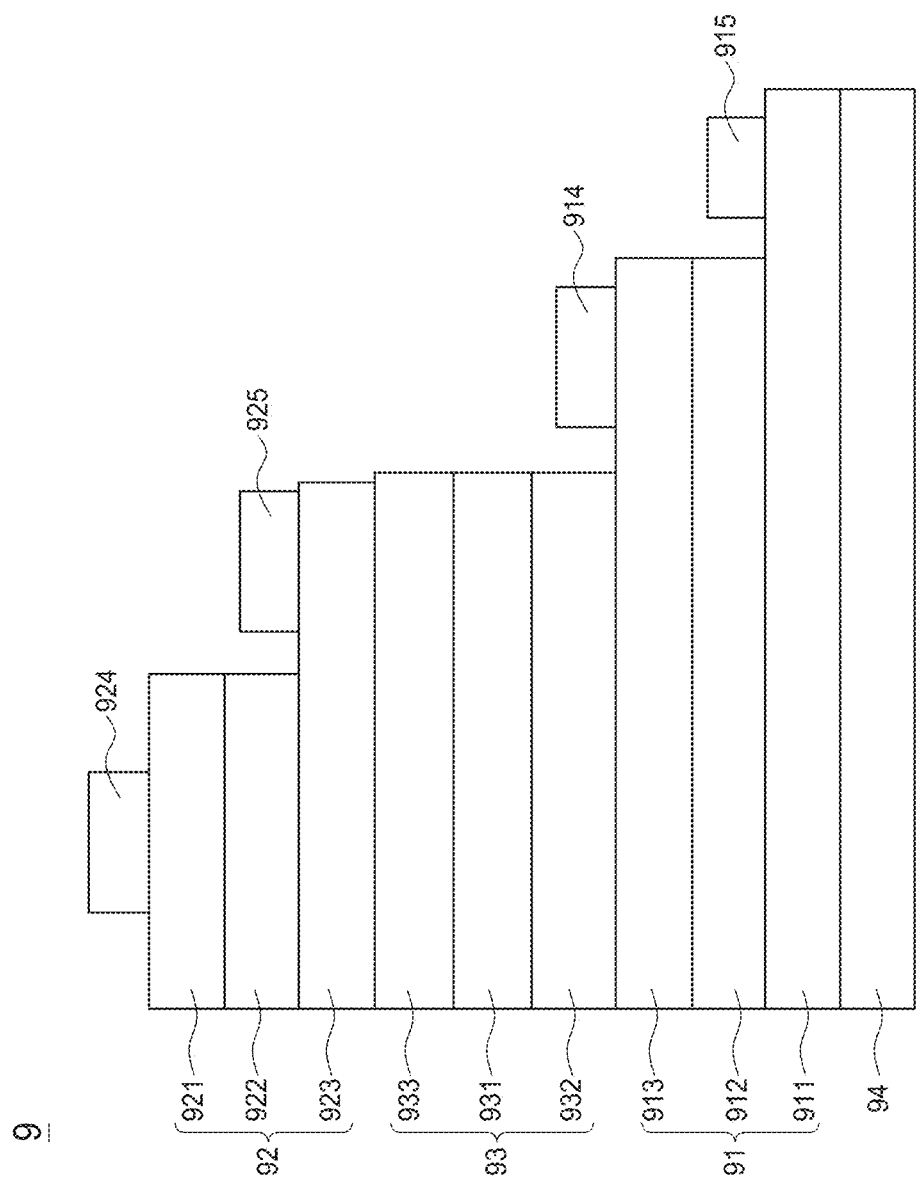
FIG. 16 is a cross-sectional view of a semiconductor device in accordance with one embodiment of the present disclosure.

FIG. 16 is a cross-sectional view of a semiconductor device 9 in accordance with an embodiment of the present disclosure. The semiconductor device 9 is a light-receiving device. The semiconductor device 9 includes a first semiconductor stack 91, a second semiconductor stack 92 on the first semiconductor stack 91, and an intermediate structure 93 between the first semiconductor stack 91 and the second semiconductor stack 92. The semiconductor device 9 further includes a substrate 94, and the first semiconductor stack 91, the intermediate structure 93 and the second semiconductor stack 92 are sequentially on the substrate 94. The first semiconductor stack 91 and the second semiconductor stack 92 have a structure same as or different from that of the first semiconductor stack 81. Specifically, the first semiconductor stack 91 includes a first-type semiconductor structure 911, an active region 912 and a second-type semiconductor structure 913 sequentially disposed on the substrate 94. The second semiconductor stack 92 includes a first-type semiconductor structure 921 away from the first semiconductor stack 91, and active region 922 and a second-type semiconductor structure 923 adjacent to the second-type semiconductor structure 913 of the first semiconductor stack 91. The active region 912 of the first semiconductor stack 91 has a band gap same as or different from that of the active region 922 of the second semiconductor stack 92. In this embodiment, the active region 912 of the first semiconductor stack 91 has a band gap smaller than that of the active region 922 of the second semiconductor stack 92, thereby being in response to different wavelengths to produce different current signal. The photocurrent producing from the first semiconductor stack 91 is conducted by a first electrode 914 and a second electrode 915 and the photocurrent producing from the second semiconductor stack 92 is conducted by a first electrode 924 and a second electrode 925. In addition, the first-type semiconductor structures 911, 912 have the same conductivity, such as n-type, and the second-type semiconductor structures 913, 923 have the same conductivity, such as p-type.

The intermediate structure includes a conducting layer 931, a first shielding layer 932 and a second shielding layer 933. The first shielding layer 932 is between the conducting layer 931 and the second-type semiconductor structure 913 of the first semiconductor stack 91 and the second shielding layer 933 is between the conducting layer 931 and the second-type semiconductor structure 923 of the second semiconductor stack 92. The conducting layer 931 includes metal, alloy or semiconductor with highly doping concentration. When the conducting layer 931 is semiconductor with highly doping concentration, the conducting layer 931 has the type same as or different from that of the first-type semiconductor structure.

When one of the semiconductor stacks absorbs a light, the electron-hole pairs are generated therein and induce charges in the intermediate structure 9. If the induced charges accumulate in the intermediate structure 9, the semiconductor device 9 is adversely affected. The conducting layer 931 is provided to prevent electric charges from accumulating in the intermediate structure 9. Especially, when the first semiconductor stack 91 and the second semiconductor stack 92 produce photocurrents in response to two lights with different frequencies, the conducting layer 931 can avoid current crosstalk. On the contrary, when the conducting layer 931 is not provided and the first semiconductor stack 91 is exposed to a light with a first frequency, an induced charge is produced in the second semiconductor stack 92 which causes a noise signal to the output signal of the second semiconductor stack 92. Briefly, if the conducting layer 931 is not provided, the first semiconductor stack 91 and the second semiconductor stack 92 interfere with each other to change frequency, amplitude or waveform of the signals produced from the absorption of lights. Moreover, the first shielding layer 932 and the second shielding layer 933 provides an electrically insulation between the first semiconductor stack 91 and the second semiconductor stack 92 for being capable of dependently controlling the first semiconductor stack 91 and the second semiconductor stack 92. In this embodiment, the doping concentration in the conducting layer 931 is larger than that in the first-type semiconductor structure 913, 923 and is larger than $1 \times 10^{17}$ cm$^{-3}$. The first shielding layer 932 and the second shielding layer 933 have a resistance larger than $10^{16}\Omega$. In addition, the intermediate structure 93 has a transmittance larger than 85% at the receiving-wave band absorbed by the first semiconductor stack 91 for passing therethrough.

In this embodiment, the first semiconductor stack 91, the intermediate structure 93 and the second semiconductor stack 92 are formed by epitaxial growth so there is no need to bond the first semiconductor stack 91 and the second semiconductor stack 92. In one embodiment, the first semiconductor stack 91, the intermediate structure 93 and the second semiconductor stack 92 are connected with each other by transferring or bonding process. In another embodiment, the intermediate structure 93 includes a first first-type semiconductor stack, a second-type semiconductor stack, and a second first-type semiconductor stack formed sequentially on the second-type semiconductor structures 913 to form a npn or pnp structure for preventing the electrical current crosstalk. The intermediate structure 93 can be disposed between the first semiconductor stack 81 and the second semiconductor stack 81a of the light-receiving devices 8a~8e or/and the second semiconductor stack 81a and the third semiconductor stack 81b of the light-receiving devices 8d~8e.

It will be apparent to those having ordinary skill in the art that various modifications and variations can be made to the devices in accordance with the present disclosure without departing from the scope or spirit of the disclosure. In view of the foregoing, it is intended that the present disclosure covers modifications and variations of this disclosure provided they fall within the scope of the following claims and their equivalents.

What is claimed is:

1. An optical sensing device, comprising:
a carrier body;
a first light-emitting device disposed on the carrier body and having a first emitting wave hand; and
a light-receiving device comprising a group III-V semiconductor material disposed on the carrier body, comprising a light-receiving surface having an area, wherein the light-receiving device is capable of receiving a first received wavelength having a largest external quantum efficiency so the ratio of the largest external quantum efficiency to the area is ≥13.

2. The optical sensing device of claim 1, wherein the light-receiving device is capable of receiving a second received wavelength having an external quantum efficiency which is 2% of the largest external quantum efficiency, and the difference between the first received wavelength and the second received wavelength is not larger than 200 nm.

3. The optical sensing device of claim 1, wherein the largest external quantum efficiency is larger than 78%.

4. The optical sensing device of claim 1, wherein the carrier body comprises a first block wall, a second block wall, and a third block wall, wherein the light-emitting device is disposed between the first block wall and the second block wall and the light-receiving device is disposed between the second block wall and the third block wall.

5. The optical sensing device of claim 4, wherein each of the first block wall and the second block wall comprises a light-reflective layer facing the light-emitting device.

6. The optical sensing device of claim 4, wherein each of the second block wall and the third block wall comprises a light-absorbing layer facing the light-receiving device.

7. The optical sensing device of claim 4, wherein the carrier body comprises a carrier plate; the light-emitting device is disposed on the carrier plate; the first block wall comprises a first inclined angle relative to the carrier plate; the second block wall comprises a second inclined angle relative to the carrier plate; and the first inclined angle is not equal to the second inclined angle.

8. The optical sensing device of claim 4, wherein the carrier body comprises a carrier plate; the light-emitting device is disposed on the carrier plate; the first block wall comprises a first inclined angle relative to the carrier plate; the second block wall comprises a second inclined angle relative to the carrier plate; and the first inclined angle is equal to the second inclined angle.

9. The optical sensing device of claim 1, wherein the light-receiving device comprises a semiconductor stack comprising a main absorption surface and an electrode pad disposed on the main absorption surface, and the area of the electrode pad is 0.08%~5% of the area of the main absorption surface.

10. The optical sensing device of claim 1, wherein the light-receiving device comprises a substrate, a first semiconductor layer, and a second semiconductor layer disposed between the substrate and the first semiconductor layer.

11. The optical sensing device of claim 10, wherein the first semiconductor layer comprises a band gap larger than that of the second semiconductor layer.

12. The optical sensing device of claim 1, wherein the light-receiving device is capable of receiving lights from different emitting wave bands.

13. The optical sensing device of claim 1, further comprising a second light-emitting device disposed on the carrier body and having a second emitting wave band larger than the first emitting wave band.

14. The optical sensing device of claim 1, wherein the light-receiving device is a photodiode and is flipped on the carrier body.

15. The optical sensing device of claim 1, wherein the first light-emitting device is a light-emitting diode or a laser-diode and is flipped on the carrier body.

16. The optical sensing device of claim 14, further comprising a supporting structure; and wherein the first light-emitting device comprises a first electrode and a second electrode located under the light-emitting device, and the first electrode and the second electrode are surrounded by the supporting structure.

17. The optical sensing device of claim 16, wherein an outer surface of the supporting structure is even to an outer surface of the first light-emitting device, and/or a lowermost surface of the supporting structure is even to lowermost surfaces of the first electrode and the second electrode.

18. The optical sensing device of claim 16, wherein the supporting structure also covers a lower surface of the first light-emitting device.

19. An optical sensing system, comprising:
an optical sensing device of claim 1;
a current control circuit coupled to the optical sensing device to drive the optical sensing device;
an amplifier coupled to the optical sensing device to receive and amplify electric signals produced from the optical sensing device; and
a signal processing module coupled to the current control circuit to output signals for the current control circuit to adjust a light intensity emitted by the light-emitting device.

20. An optical sensing system of claim 19, further comprising:
a filter coupled to an output terminal of the amplifier to eliminate an environmental noise; and an ADC circuit coupled to the output terminal of the filter to convert an analog electric signal to a digital electric signal which represents the magnitude of the light intensity.

* * * * *